US012183457B2

(12) United States Patent
Cox et al.

(10) Patent No.: US 12,183,457 B2
(45) Date of Patent: Dec. 31, 2024

(54) DIAGNOSTIC DEVICE FOR REMOTE CONSULTATIONS AND TELEMEDICINE

(71) Applicant: Medentum Innovations Inc., Coeburn, VA (US)

(72) Inventors: Nicholas Cox, Haysi, VA (US); Grayson Martin, Dante, VA (US); Christopher Owens, Birchleaf, VA (US); David Owens, Birchleaf, VA (US); Starla Kiser, Wise, VA (US); Nicolle Corner, Fairfax Station, VA (US); Vivek Ranjit Shinde Patil, Arlington, VA (US)

(73) Assignee: Medentum Innovations Inc., Coeburn, VA (US)

( * ) Notice: Subject to any disclaimer, the term of this patent is extended or adjusted under 35 U.S.C. 154(b) by 0 days.

(21) Appl. No.: 17/215,044

(22) Filed: Mar. 29, 2021

(65) Prior Publication Data

US 2022/0005601 A1 Jan. 6, 2022

Related U.S. Application Data

(60) Provisional application No. 63/048,094, filed on Jul. 4, 2020.

(51) Int. Cl.
*G16H 10/60* (2018.01)
*A61B 5/00* (2006.01)
(Continued)

(52) U.S. Cl.
CPC ........... *G16H 40/67* (2018.01); *A61B 5/0022* (2013.01); *A61B 5/0077* (2013.01);
(Continued)

(58) Field of Classification Search
CPC ....... G06Q 50/22–24; G06Q 50/20–26; G16H 40/67; G16H 40/20; G16H 10/20;
(Continued)

(56) References Cited

U.S. PATENT DOCUMENTS 7,346,174 B1 * 3/2008 Smith ................... G16H 40/63
600/528
2003/0191669 A1 * 10/2003 Fitzgerald ............ G16H 70/20
707/999.1
(Continued)

FOREIGN PATENT DOCUMENTS

GB 2586673 A * 3/2021 ........... A61B 5/0816
WO WO-2017075601 A1 * 5/2017 ........... A61B 5/7264

OTHER PUBLICATIONS

S.B. Kotsiantis, "Supervised Machine Learning: A Review of Classification Techniques", Jul. 16, 2007, Informatica 31 (2007) 249-268, all pages. (Year: 2007).*
(Continued)

*Primary Examiner* — Christopher L Gilligan
*Assistant Examiner* — Jessica Marie Webb
(74) *Attorney, Agent, or Firm* — Sheppard Mullin Richter & Hampton LLP

(57) ABSTRACT

A method of obtaining a clinical assessment of a user of a user device may include obtaining, by the user device and from a hand-held diagnostic device configured to communicate with the user device, first diagnostic information of the user obtained by one or more sensors of the hand-held diagnostic device; obtaining, by the user device, second diagnostic information based on a user input of the second diagnostic information via the user device; obtaining, by the user device and using an artificial intelligence (AI) model, the clinical assessment based on the first diagnostic information and the second diagnostic information; and display-
(Continued)

ing, by the user device, the clinical assessment to permit the user to visualize the clinical assessment.

26 Claims, 31 Drawing Sheets

(51) Int. Cl.
| | |
|---|---|
| A61B 5/0205 | (2006.01) |
| A61B 7/04 | (2006.01) |
| G16H 10/20 | (2018.01) |
| G16H 15/00 | (2018.01) |
| G16H 30/20 | (2018.01) |
| G16H 40/20 | (2018.01) |
| G16H 40/67 | (2018.01) |
| G16H 50/20 | (2018.01) |
| G16H 50/30 | (2018.01) |
| G16H 80/00 | (2018.01) |
| H04N 7/18 | (2006.01) |
| A61B 5/021 | (2006.01) |
| A61B 5/0245 | (2006.01) |
| A61B 5/08 | (2006.01) |
| A61B 5/1455 | (2006.01) |

(52) U.S. Cl.
CPC ........ *A61B 5/02055* (2013.01); *A61B 5/7264* (2013.01); *A61B 5/742* (2013.01); *A61B 7/04* (2013.01); *G16H 10/20* (2018.01); *G16H 10/60* (2018.01); *G16H 15/00* (2018.01); *G16H 30/20* (2018.01); *G16H 40/20* (2018.01); *G16H 50/20* (2018.01); *G16H 50/30* (2018.01); *G16H 80/00* (2018.01); *H04N 7/185* (2013.01); *A61B 5/021* (2013.01); *A61B 5/0245* (2013.01); *A61B 5/0816* (2013.01); *A61B 5/14552* (2013.01)

(58) Field of Classification Search
CPC ........ G16H 10/60; G16H 15/00; G16H 30/20; G16H 50/20; G16H 50/30; H04N 7/185
See application file for complete search history.

(56) References Cited

U.S. PATENT DOCUMENTS

| | | | |
|---|---|---|---|
| 2009/0326982 A1* | 12/2009 | Deobhakta | G16H 10/60 |
| | | | 705/3 |
| 2013/0211265 A1 | 8/2013 | Bedingham et al. | |
| 2014/0155755 A1* | 6/2014 | Pinter | A61B 5/7264 |
| | | | 600/474 |
| 2014/0187890 A1* | 7/2014 | Mensinger | A61B 5/742 |
| | | | 600/365 |
| 2016/0196389 A1* | 7/2016 | Moturu | G16H 50/20 |
| | | | 705/2 |
| 2016/0296200 A1 | 10/2016 | Hinojosa | |
| 2017/0112439 A1 | 4/2017 | Dubin et al. | |
| 2017/0220745 A1* | 8/2017 | Lee | G16H 10/60 |
| 2017/0235905 A1* | 8/2017 | Santiago, Jr. | G16H 10/60 |
| | | | 705/2 |
| 2018/0122509 A1* | 5/2018 | Christiansson | G16H 10/60 |
| 2018/0192965 A1 | 7/2018 | Rose et al. | |
| 2018/0254103 A1* | 9/2018 | Jung | G06F 16/90335 |
| 2018/0308565 A1 | 10/2018 | Pinter et al. | |
| 2018/0315182 A1* | 11/2018 | Rapaka | G06T 7/0012 |
| 2018/0353073 A1* | 12/2018 | Boucher | A61B 5/05 |
| 2019/0150849 A1* | 5/2019 | Yorke | A61B 5/7275 |
| 2019/0320900 A1 | 10/2019 | Majmudar | |
| 2019/0380582 A1* | 12/2019 | Galgalikar | A61B 5/0006 |
| 2020/0029837 A1* | 1/2020 | Joudi | A61B 5/0086 |
| 2020/0273581 A1* | 8/2020 | Wolf | G16H 40/63 |
| 2021/0145352 A1* | 5/2021 | Rogers | A61B 5/150022 |

OTHER PUBLICATIONS

L. C. Rabelo, A. Jones and Y. Yih, "Development of a real-time learning scheduler using reinforcement learning concepts," Proceedings of 1994 9th IEEE International Symposium on Intelligent Control, Columbus, OH, USA, 1994, pp. 291-296, doi: 10.1109/ISIC.1994.367802. (Year: 1994).*

Nakano H, Furukawa T, Tanigawa T. Tracheal Sound Analysis Using a Deep Neural Network to Detect Sleep Apnea. J Clin Sleep Med. 2019;15(8):1125-1133. doi:10.5664/jcsm.7804 (Year: 2019).*

Mark Hall, Eibe Frank, Geoffrey Holmes, Bernhard Pfahringer, Peter Reutemann, Ian H. Witten (2009); The WEKA Data Mining Software: An Update; SIGKDD Explorations, vol. 11, Issue 1. https://www.researchgate.net/publication/221900777_The_WEKA_data_mining_software_An_update (Year: 2009).*

Bouckaert et al, WEKA Manual for Version 3-8-3, 2018, The University of Waikato, all pages. https://user.eng.umd.edu/~austin/ence688p.d/handouts/ (Year: 2018).*

* cited by examiner

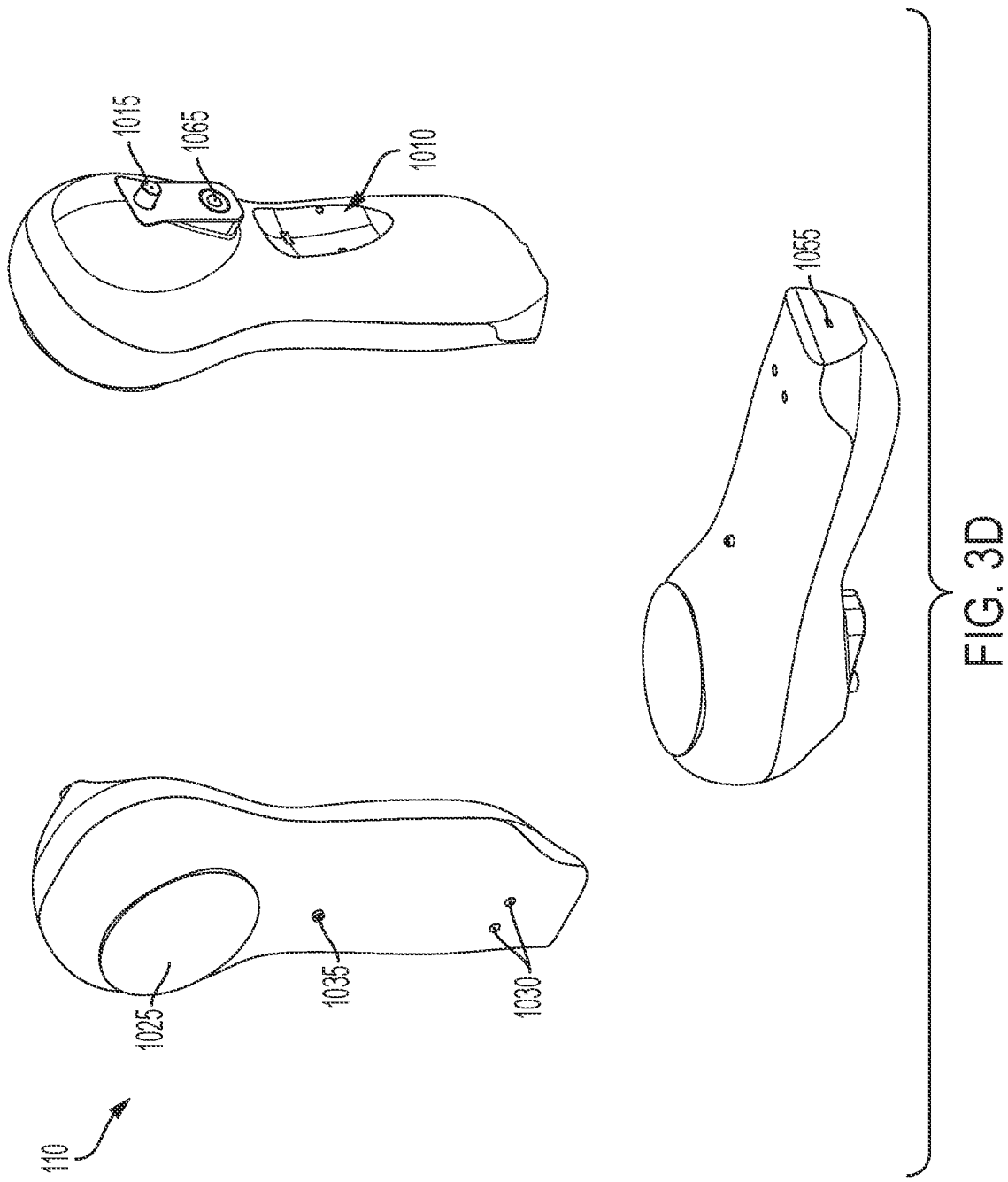

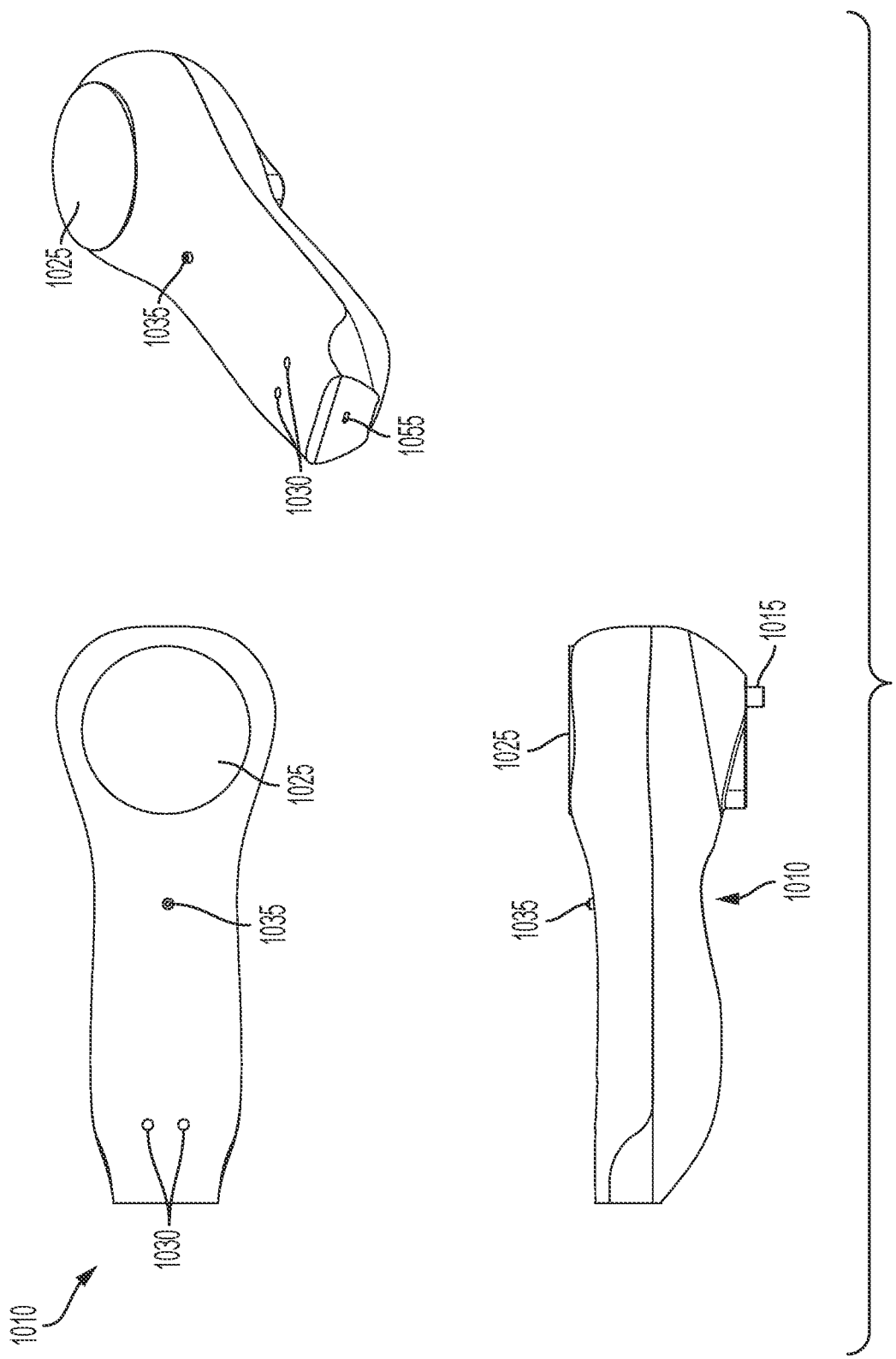

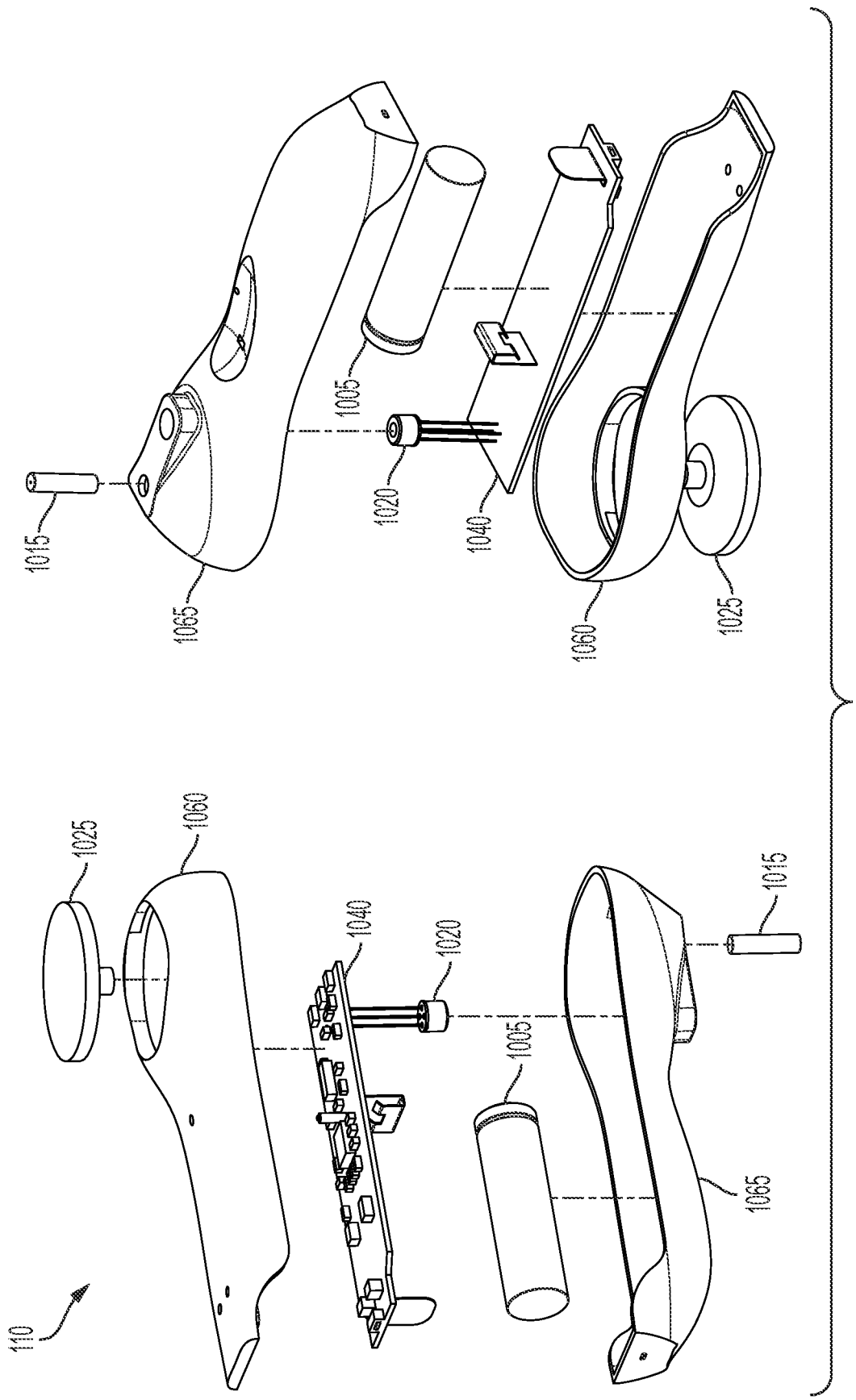

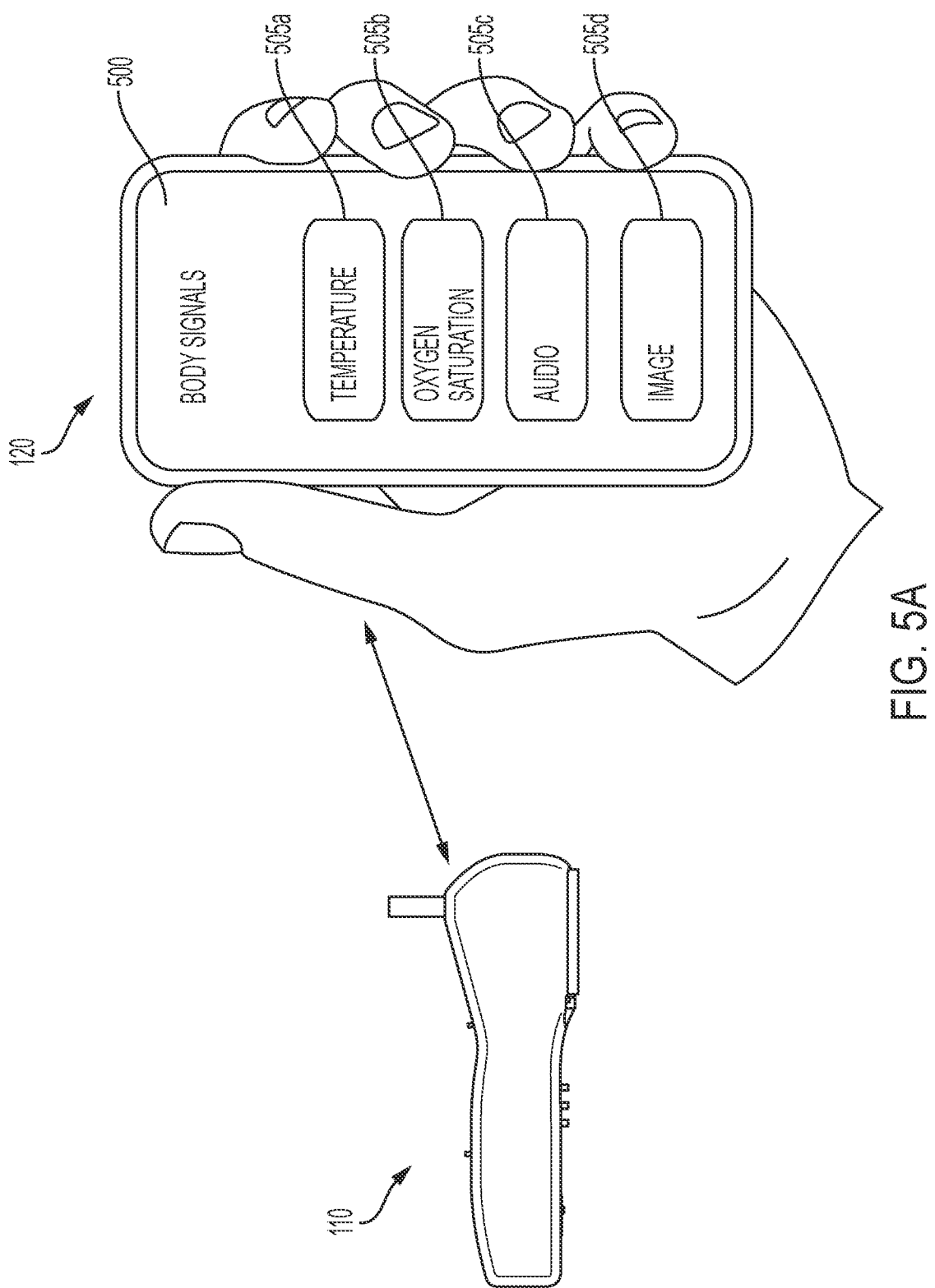

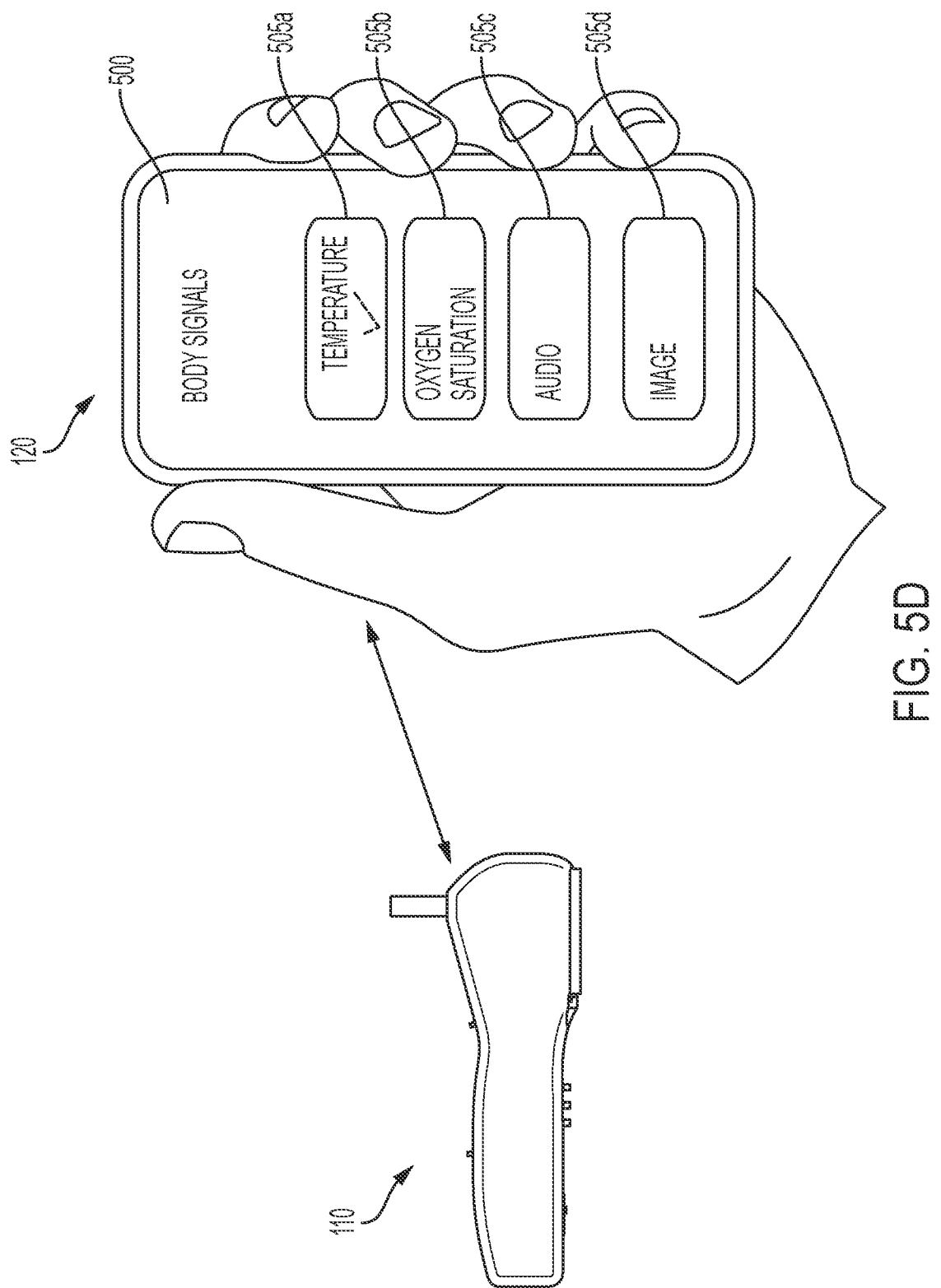

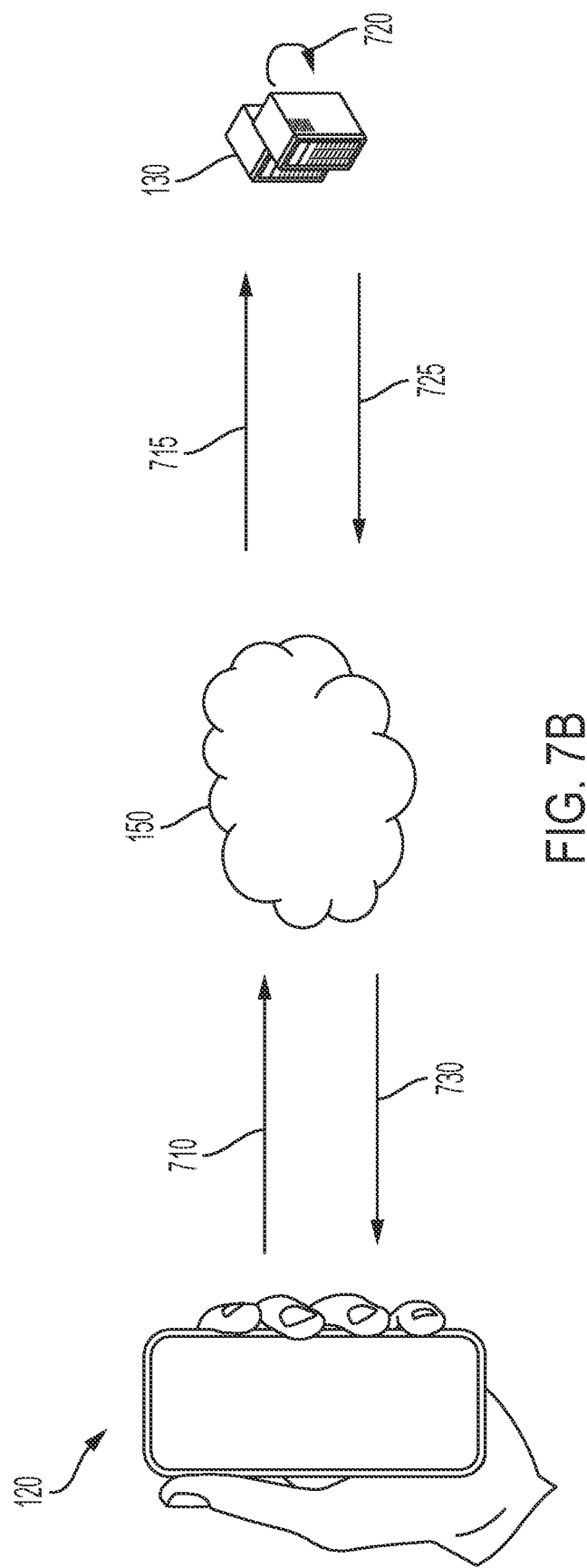

DIAGNOSTIC DEVICE FOR REMOTE CONSULTATIONS AND TELEMEDICINE

CROSS-REFERENCE TO RELATED APPLICATION(S)

This application is based on and claims priority under 35 U.S.C. § 119 to U.S. Provisional Patent Application No. 63/048,094, filed on Jul. 4, 2020, in the U.S. Patent & Trademark Office, the disclosure of which is incorporated by reference herein in its entirety.

BACKGROUND

1. Field

The present disclosure relates to a diagnostic system including a diagnostic device configured to obtain diagnostic information of a user, a user device configured to communicate with the diagnostic device and a platform, and the platform configured to obtain a clinical assessment based on the diagnostic device.

2. Description of Related Art

The rapid growth in telemedicine warrants a more comprehensive data-centric online patient-physician engagement. Most telehealth consultations are qualitative in nature. For example, a patient typically verbally describes their symptoms to a physician, and the physician makes a corresponding diagnosis. Sometimes, these "qualitative" examinations lead to incomplete or erroneous diagnoses. Other times, these telehealth consultations require follow up visits to perform disease testing or in-person physician consultations. This presents a substantial burden in rural, and some non-urban, areas given the low density of medical infrastructure and the need for patients to travel long distances to access high-quality healthcare.

SUMMARY

According to an embodiment, a method of obtaining a clinical assessment of a user of a user device may include obtaining, by the user device and from a hand-held diagnostic device configured to communicate with the user device, first diagnostic information of the user measured by one or more sensors of the hand-held diagnostic device; obtaining, by the user device, second diagnostic information based on a user input of the second diagnostic information via the user device; obtaining, by the user device and using an artificial intelligence (AI) model, the clinical assessment based on the first diagnostic information and the second diagnostic information; and displaying, by the user device, the clinical assessment to permit the user to visualize the clinical assessment.

According to an embodiment, a user device may be configured to obtain a clinical assessment of a user. The user device may include a memory configured to store instructions; and a processor configured to execute the instructions to obtain, from a hand-held diagnostic device configured to communicate with the user device, first diagnostic information of the user measured by one or more sensors of the hand-held diagnostic device; obtain second diagnostic information based on a user input of the second diagnostic information via the user device; obtain, using an artificial intelligence (AI) model, the clinical assessment based on the first diagnostic information and the second diagnostic information; and control a display of the user device to display the clinical assessment to permit the user to visualize the clinical assessment.

According to an embodiment, a non-transitory computer-readable medium may store one or more instructions that, when executed by one or more processors of a user device configured to obtain a clinical assessment of a user, cause the one or more processors to obtain, from a hand-held diagnostic device configured to communicate with the user device, first diagnostic information of the user measured by one or more sensors of the hand-held diagnostic device; obtain second diagnostic information based on a user input of the second diagnostic information via the user device; obtain, using an artificial intelligence (AI) model, the clinical assessment based on the first diagnostic information and the second diagnostic information; and control a display of the user device to display the clinical assessment to permit the user to visualize the clinical assessment.

Additional aspects will be set forth in part in the description that follows and, in part, will be apparent from the description, or may be learned by practice of the presented embodiments of the disclosure.

BRIEF DESCRIPTION OF THE DRAWINGS

The above and other aspects, features, and aspects of embodiments of the disclosure will be more apparent from the following description taken in conjunction with the accompanying drawings, in which:

FIGS. 5A-5G are diagrams of a user interface of the diagnostic application according to an embodiment;

FIGS. 7A-7C are diagrams of a user interface of the diagnostic application according to an embodiment.

DETAILED DESCRIPTION

The following detailed description of example embodiments refers to the accompanying drawings. The same reference numbers in different drawings may identify the same or similar elements.

According to an example embodiment, a multi-component, non-invasive diagnostic device utilizes low-cost sensors to pick up the body's biomechanical, bioelectrical and biophysical signals. The device is configured to record and transmit a wide array of signals such as vibrations, pulses, pressure changes, electrical changes, heat, and optical or acoustic reflectance. The sensors (from the handheld device) and component software are configured to convert recorded signals into digital readouts. These digital readouts provide both traditional physiological outputs but can also be combined or used creatively to provide novel digital biomarkers that reflect a person's physiological or pathological state.

Traditional physiological outputs include blood pressure, temperature, heart rate, and oxygen saturation and are measured using dedicated sensors located on the handheld device. Sensors may also be combined creatively to provide readouts beyond their traditional indications. For example, blood pressure is typically assessed using a traditional sphygmomanometer. The combination of pressure/ECG/PCG sensors incorporated into the handheld device provides similar blood pressure readouts and trends. Blood pressure predictions can also be inferred from visualizations of pressure wave amplitudes collected from pressure sensors placed on the chest. In contrast, a temperature sensor applied to the forehead might predict core body temperature, or it might predict underlying soft tissue infection if applied to the skin or wound (novel digital biomarker).

Importantly, signals collected from sensors are conditioned or optimized by software programs. For example, audio signals collected from the digital stethoscope are processed by filtering algorithms to eliminate background noise and provide clear and audible heart and lung sounds. The processed sensor data is combined with clinical information and diagnostic data collected by the device's companion smartphone app, and analyzed using AI/ML algorithms. AI/ML algorithms utilizing different data sources (sensor, clinical information, demographic and/or diagnosis) identify signal patterns and allow for the creation of novel digital biomarkers/outputs that predict clinical outcomes. For example, AI/ML classification of filtered heart sounds combined with patient symptom data and medical history (e.g., heart disease) may predict cardiac anomalies and guide patients to better triage and treatment.

Figure 1:
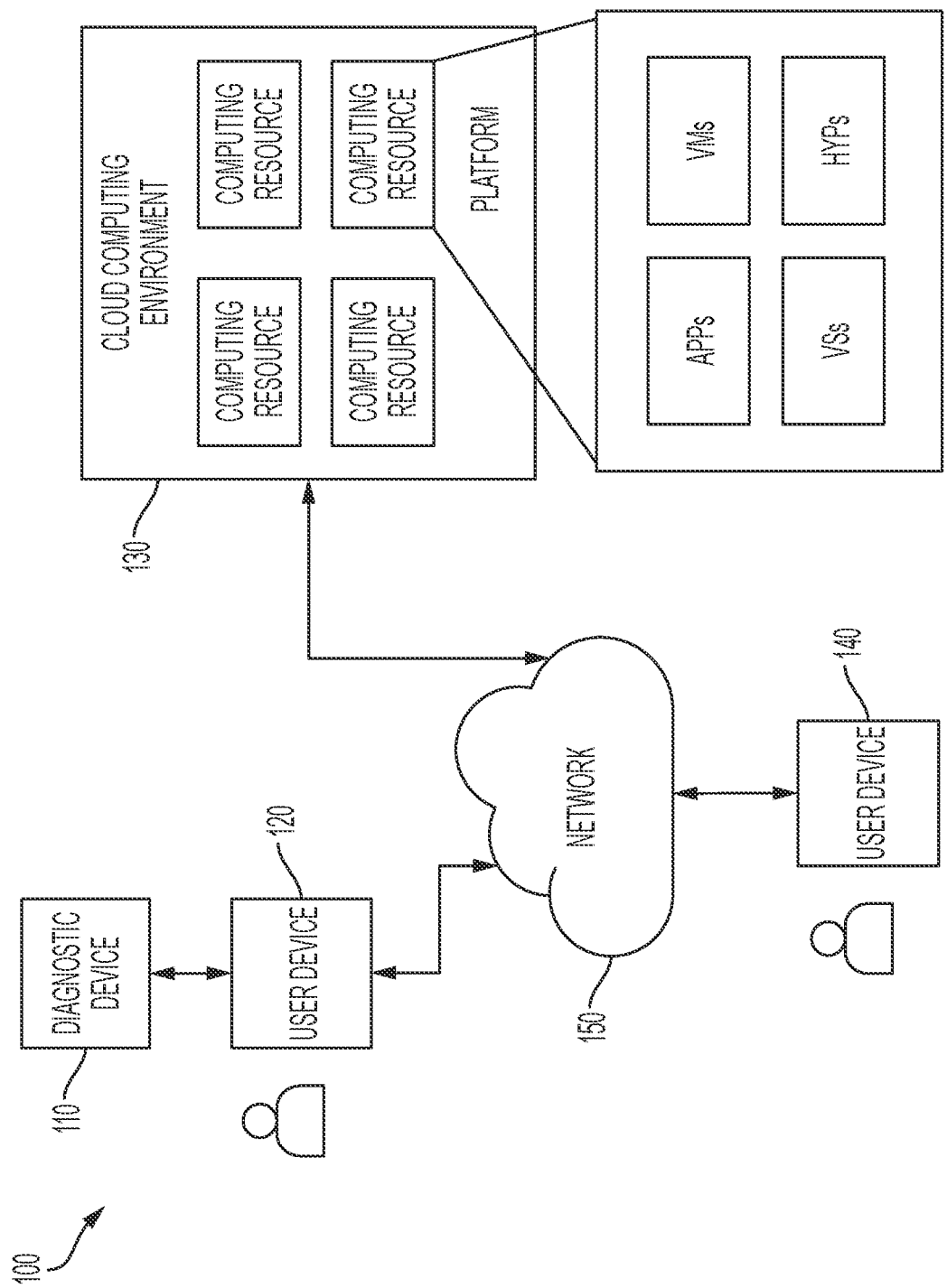
FIG. 1 is a diagram of a diagnostic system according to an embodiment.

FIG. 1 is a diagram of a diagnostic system according to an embodiment. As shown in FIG. 1, a diagnostic system 100 may include a diagnostic device 110, a user device 120, a platform 130, a user device 140, and a network 150. Devices of the diagnostic system 100 may interconnect via wired connections, wireless connections, or a combination of wired and wireless connections.

Diagnostic device 110 is configured to obtain diagnostic information of a user, and provide the diagnostic information to the user device 120, the platform 130, and/or the user device 140. The diagnostic device 110 is configured to receive a clinical assessment from the user device 120, the platform 130, and/or the user device 140, and display the clinical assessment.

As used herein, "diagnostic information" may refer to information that permits a diagnosis of a user. For example, the diagnostic information may include bio-information of a user (e.g., an oxygen saturation level, a temperature, a heart rate, a blood pressure, a calorie level, etc.), audio information of the user (e.g., a heart sound, a lung sound, etc.), image or video information of the user, characteristic information of a user (e.g., a name, an address, an occupation, a marital status, a date of birth, a gender, a weight, a height, etc.), body signals, clinical information (e.g., symptoms, medical history, demographics, and laboratory result information), allergy information of the user, vaccination information of the user, chronic or pre-existing condition information of the user, health history information of the user, family health history information of the user, etc.

As used herein, "body signal(s)" refers to any biomechanical, bioelectrical, biophysical, or other signals measured by mechanical or digital means that are used to reflect a body's physiological or pathological state. Body signals is an all-encompassing term to include traditional vital signs (e.g., heart rate, blood pressure, oxygen saturation, temperature, EKG), body sounds (e.g., heart, lung, gut sounds) and also novel biomarkers. "Digital means" refers to a component configured to obtain any body signals from sensors placed on the body. "Novel biomarkers" refers to undiscovered body signals, combinations of body signals, or signal patterns collected from the digital sensors that will be and can be used to predict a body's physiological or pathological state.

As used herein, "clinical assessment" may refer to information that is associated with a diagnosis of the user. For example, the diagnosis information may include information that identifies a particular health condition of the user, recommendation information that identifies a health plan of the user, warning information that identifies a health risk of the user, triage information that identifies an urgency level associated with a diagnosis, etc.

The diagnostic device 110, the user device 120, the platform 130, and the user device 140 may execute and/or access an application (hereinafter "diagnostic application") that permits one or more of the foregoing device(s) to obtain diagnostic information of a user, determine a clinical assessment of the user, and display the clinical assessment of the user.

Based on installing a client-version of the diagnostic application (e.g., an IOS® application, an ANDROID® application, etc.), the user device 120 may execute the diagnostic application, and display a user interface that prompts the user to generate a user profile. For example, the user device 120 may display a user interface that prompts the user for diagnostic information (e.g., a name, a weight, a height, health history information, etc.).

The user interface may include a set of checklists, menus, etc., that permit the user to generate the user profile and input the diagnostic information. Additionally, the user device 120 may provide a virtual assistant (e.g., an intelligent virtual assistant (IVA), an intelligent personal assistant (IPA), etc.) that may prompt the user for information, respond to user inquiries, etc.

The platform 130 may execute a back-end version of the diagnostic application that is configured to obtain diagnostic information from the user device 120 (e.g., based on a user input, based on components of the diagnostic device 110 obtaining diagnostic information, etc.), store the diagnostic information, obtain a clinical assessment based on the diagnostic information, and provide the clinical assessment to the user device 120 (e.g., provide the clinical assessment to the client-version of the diagnostic application).

In some embodiments, the platform 130 may obtain the clinical assessment from the user device 140. For example, the platform 130 may provide the diagnostic information to the user device 140, and may receive the clinical assessment from the user device 140. In this case, a doctor may view the diagnostic information via the user device 140, input the clinical assessment via the user device 140, and provide the clinical assessment to the user device 120 via the user device 140 and the platform 130.

In other embodiments, the platform 130 may obtain the clinical assessment based on determining the clinical assessment. For example, the platform 130 may input the diagnostic information into a model, and determine the clinical assessment based on an output of the model.

User device 120 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. The user device 120 may be associated with a user of the diagnostic system 100, such as a patient, an individual, etc.

Platform 130 may include a cloud server or a group of cloud servers. Platform 130 may be designed to be modular such that certain software components may be swapped in or out depending on a particular need. As such, platform 130 may be easily and/or quickly reconfigured for different uses.

As shown, the platform 130 may be hosted in cloud computing environment. Although embodiments described herein describe the platform 130 as being hosted in a cloud computing environment, the platform 130 might not be cloud-based or may be partially cloud-based.

The cloud computing environment includes an environment that hosts the platform 130. The cloud computing environment may provide computation, software, data access, storage, etc. services that do not require end-user (e.g., a user of the user device 120 and/or a user of the user device 140) knowledge of a physical location and configuration of system(s) and/or device(s) that hosts the platform 130. As shown, the cloud computing environment may include a group of computing resources (referred to collectively as "the computing resources" and individually as "the computing resource").

The computing resource includes one or more personal computers, workstation computers, server devices, or other types of computation and/or communication devices. The computing resource may host the platform 130. The cloud resources may include compute instances executing in the computing resource, storage devices provided in the computing resource, data transfer devices provided by the computing resource, etc. The computing resource may communicate with other computing resources via wired connections, wireless connections, or a combination of wired and wireless connections.

As further shown in FIG. 1, the computing resource includes a group of cloud resources, such as one or more applications ("APPs"), one or more virtual machines ("VMs"), virtualized storage ("VSs"), one or more hypervisors ("HYPs"), or the like.

The application includes one or more software applications that may be provided to or accessed by the user device 120 and/or the user device 140. The application may eliminate a need to install and execute the software applications on the user device 120 and/or the user device 140. For example, the application may include software associated with the platform 130 and/or any other software capable of being provided via the cloud computing environment. One application may send/receive information to/from one or more other applications, via a virtual machine.

The virtual machine includes a software implementation of a machine (e.g., a computer) that executes programs like a physical machine. The virtual machine may be either a system virtual machine or a process virtual machine, depending upon use and degree of correspondence to any real machine by the virtual machine. A system virtual machine may provide a complete system platform that supports execution of a complete operating system ("OS"). A process virtual machine may execute a single program, and may support a single process. The virtual machine may execute on behalf of a user (e.g., user device 120 and/or user device 140), and may manage infrastructure of the cloud computing environment, such as data management, synchronization, or long-duration data transfers.

The virtualized storage includes one or more storage systems and/or one or more devices that use virtualization techniques within the storage systems or devices of the computing resource. Within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

The hypervisor may provide hardware virtualization techniques that allow multiple operating systems (e.g., "guest operating systems") to execute concurrently on a host computer, such as the computing resource. The hypervisor may present a virtual operating platform to the guest operating systems, and may manage the execution of the guest operating systems. Multiple instances of a variety of operating systems may share virtualized hardware resources.

User device 140 may include a computing device (e.g., a desktop computer, a laptop computer, a tablet computer, a handheld computer, a smart speaker, a server, etc.), a mobile phone (e.g., a smart phone, a radiotelephone, etc.), a wearable device (e.g., a pair of smart glasses or a smart watch), or a similar device. The user device 140 may be associated with a user of the diagnostic system 100, such as a doctor, a medical practitioner, a physician, etc.

Network 150 includes one or more wired and/or wireless networks. For example, network 150 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, or the like, and/or a combination of these or other types of networks.

The number and arrangement of devices and networks shown in FIG. 1 are provided as an example. In practice, there may be additional devices and/or networks, fewer devices and/or networks, different devices and/or networks, or differently arranged devices and/or networks than those shown in FIG. 1. Furthermore, two or more devices shown in FIG. 1 may be implemented within a single device, or a single device shown in FIG. 1 may be implemented as multiple, distributed devices. A set of devices (e.g., one or more devices) of the diagnostic system 100 may perform one or more functions described as being performed by another set of devices of the diagnostic system 100.

Figure 2:
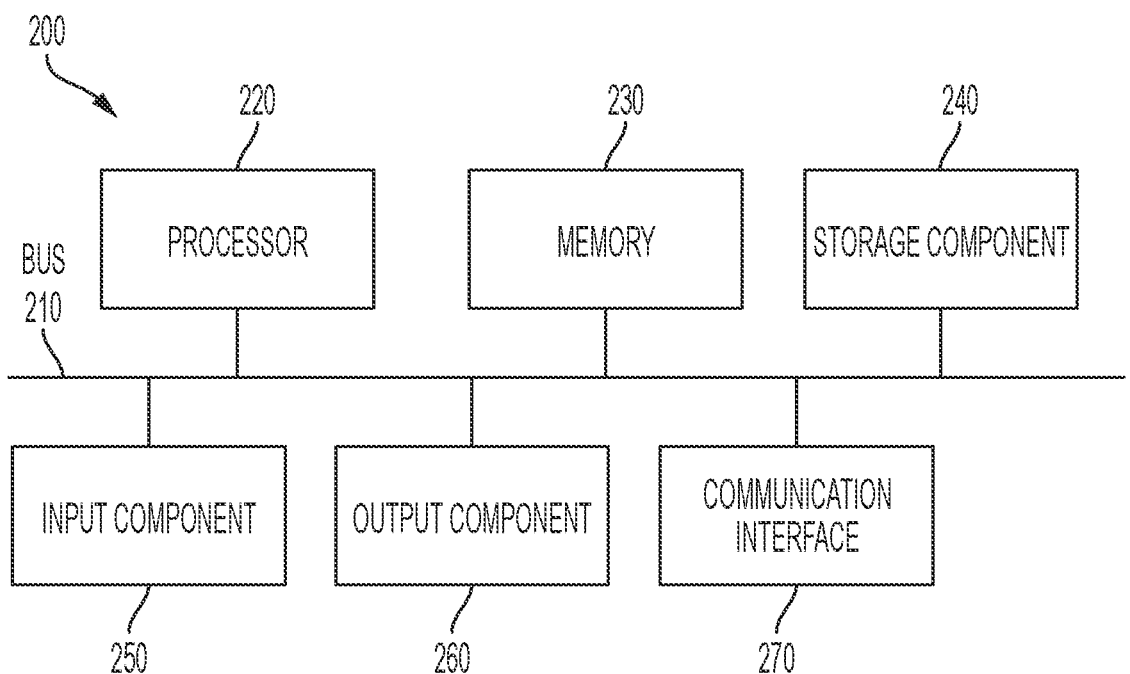
FIG. 2 is a diagram of example components of one or more devices of FIG. 1 according to an embodiment.

FIG. 2 is a diagram of example components of one or more devices of FIG. 1 according to an embodiment. Device 200 may correspond to the diagnostic device 110, the user device 120, the platform 130, and/or the user device 140. As shown in FIG. 2, the device 200 may include a bus 210, a processor 220, a memory 230, a storage component 240, an input component 250, an output component 260, and a communication interface 270.

Bus 210 includes a component that permits communication among the components of the device 200. Processor 220 is implemented in hardware, firmware, or a combination of hardware and software. Processor 220 is a central processing unit (CPU), a microcontroller unit, (MCU), a graphics processing unit (GPU), an accelerated processing unit (APU), a microprocessor, a microcontroller, a microcontroller unit (MCU), a digital signal processor (DSP), a field-programmable gate array (FPGA), an application-specific integrated circuit (ASIC), or another type of processing component. The processor 220 includes one or more processors capable of being programmed to perform a function. Memory 230 includes a random access memory (RAM), a read only memory (ROM), and/or another type of dynamic or static storage device (e.g., a flash memory, a magnetic memory, and/or an optical memory) that stores information and/or instructions for use by the processor 220.

Storage component 240 stores information and/or software related to the operation and use of the device 200. For example, the storage component 240 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 250 includes a component that permits the device 200 to receive information, such as via user input (e.g., a touch screen display, a keyboard, a keypad, a mouse, a button, a switch, and/or a microphone). The input component 250 may include a sensor for sensing information (e.g., a global positioning system (GPS) component, an accelerometer, a gyroscope, and/or an actuator). The output component 260 includes a component that provides output information from the device 200 (e.g., a display, a speaker, and/or one or more light-emitting diodes (LEDs)).

Communication interface 270 includes a transceiver-like component (e.g., a transceiver and/or a separate receiver and transmitter) that enables the device 200 to communicate with other devices, such as via a wired connection, a wireless connection, or a combination of wired and wireless connections. The communication interface 270 may permit the device 200 to receive information from another device and/or provide information to another device. For example, the communication interface 270 may include an Ethernet interface, an optical interface, a coaxial interface, an infrared interface, a radio frequency (RF) interface, a universal serial bus (USB) interface, a Wi-Fi interface, a Bluetooth interface, a cellular network interface, or the like.

The device 200 may perform one or more processes described herein. The device 200 may perform these processes in response to the processor 220 executing software instructions stored by a non-transitory computer-readable medium, such as the memory 230 and/or the storage component 240. A computer-readable medium is defined herein as a non-transitory memory device. A memory device includes memory space within a single physical storage device or memory space spread across multiple physical storage devices.

Software instructions may be read into the memory 230 and/or the storage component 240 from another computer-readable medium or from another device via the communication interface 270. When executed, software instructions stored in the memory 230 and/or the storage component 240 may cause the processor 220 to perform one or more processes described herein.

Hardwired circuitry may be used in place of or in combination with software instructions to perform one or more processes described herein. Thus, embodiments described herein are not limited to any specific combination of hardware circuitry and software.

The number and arrangement of components shown in FIG. 2 are provided as an example. In practice, the device 200 may include additional components, fewer components, different components, or differently arranged components than those shown in FIG. 2. A set of components (e.g., one or more components) of the device 200 may perform one or more functions described as being performed by another set of components of the device 200.

Figure 3A:
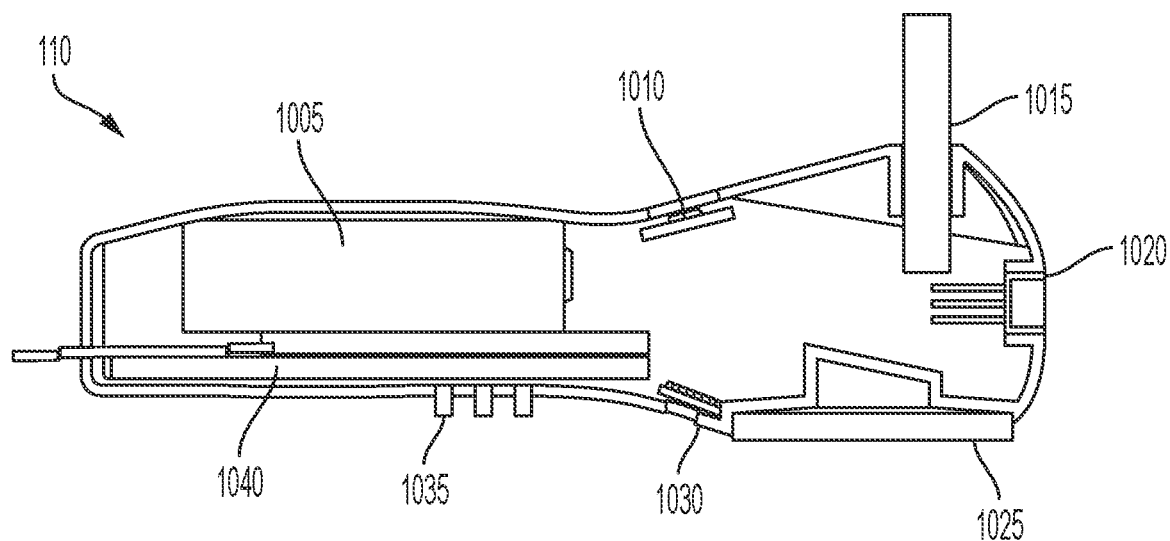
FIGS. 3A-3J are diagrams of a diagnostic device according to various embodiments.

FIGS. 3A-3J are diagrams of a diagnostic device according to various embodiments. As shown in FIG. 3A, the diagnostic device 110 includes a battery 1005, a pulse oximeter 1010, a camera 1015, a temperature sensor 1020, a stethoscope 1025, a display 1030, an input component 1035, and a controller 1040.

Figure 3B:
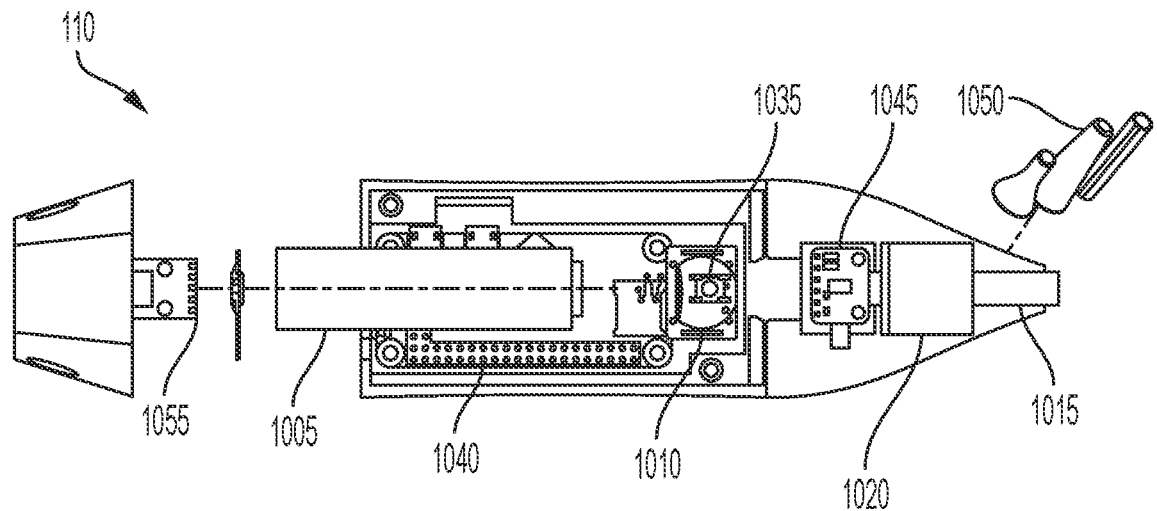
Figure 3C:
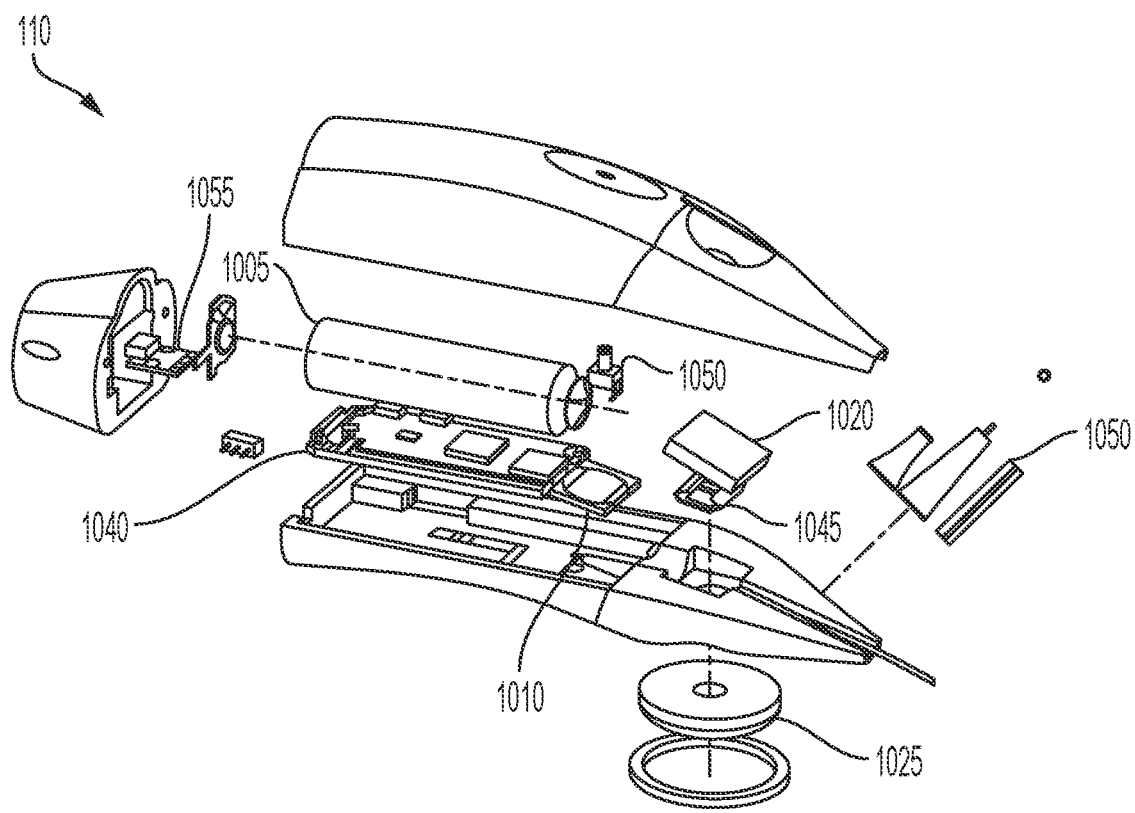
Figure 3F:
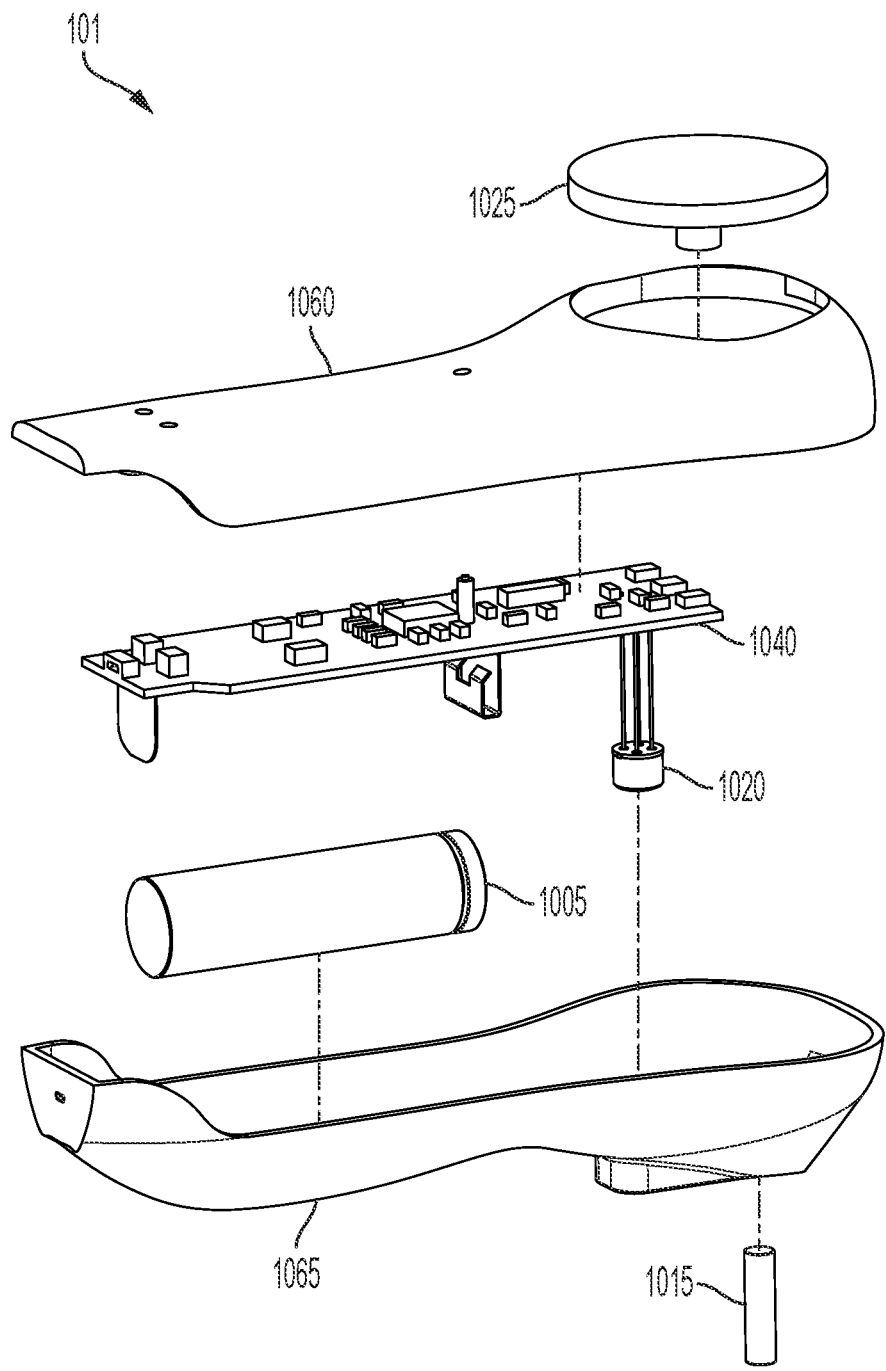
Figure 3H:
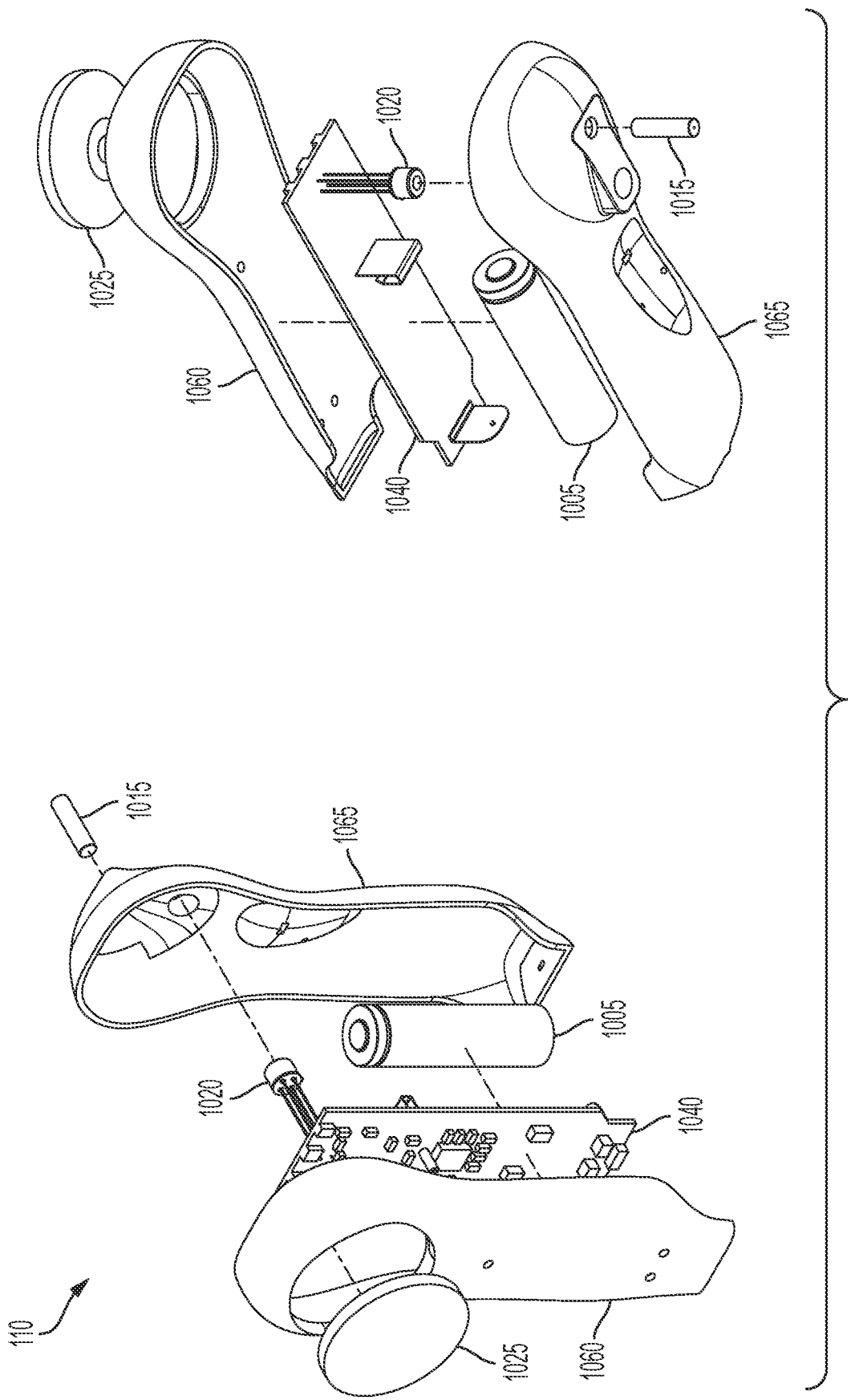
Figure 3:
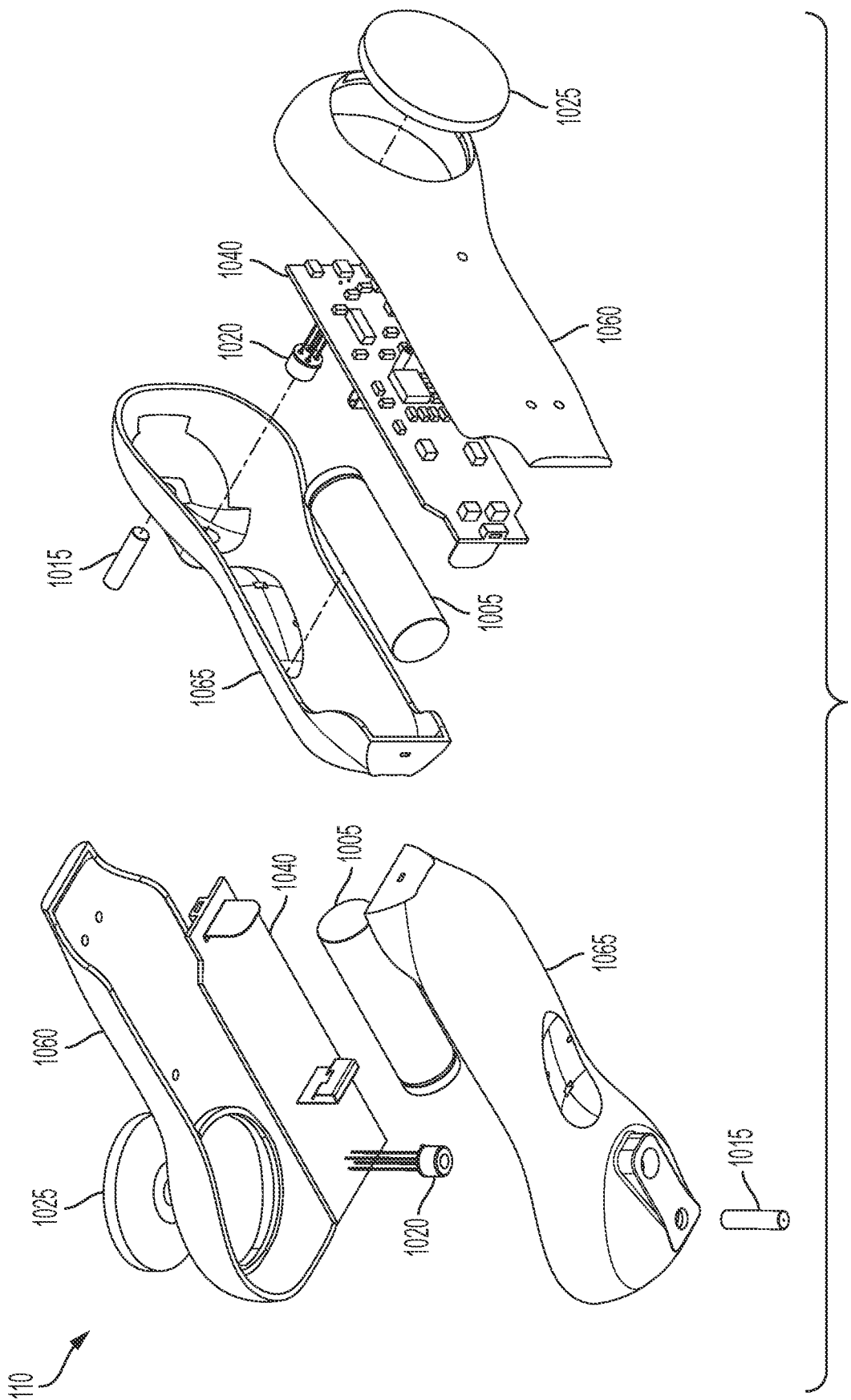
Figure 3J:
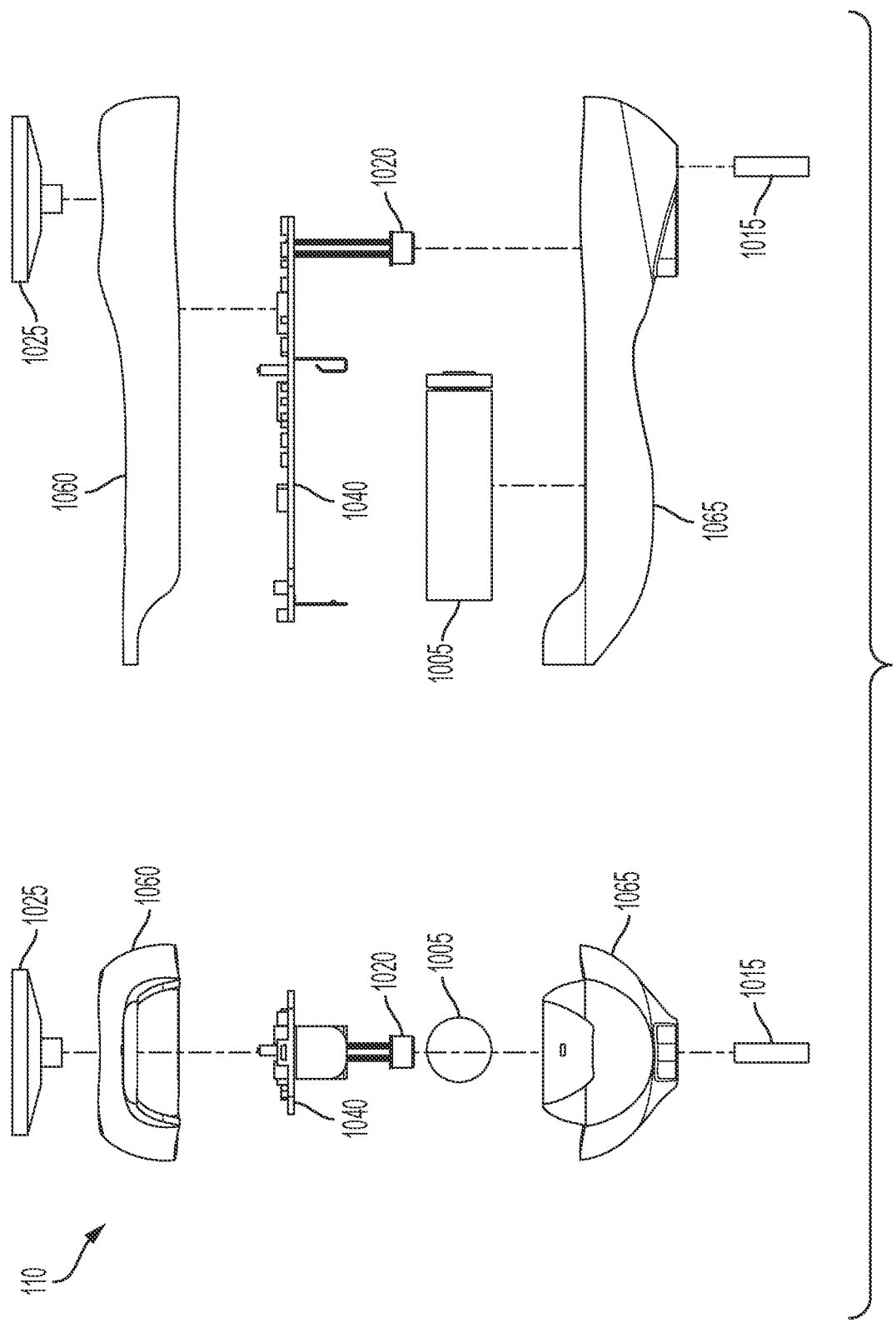

As shown in FIGS. 3B and 3C, a diagnostic device 110 according to another embodiment includes a battery 1005, a pulse oximeter 1010, a camera 1015, a temperature sensor 1020, a stethoscope 1025, an input component 1035, a controller 1040, a microphone 1045, a camera cover 1050, and a charge input 1055.

As shown in FIGS. 3D-3J, a diagnostic device 110 according to another embodiment includes a battery 1005, a pulse oximeter 1010, a camera 1015, a temperature sensor 1020, a stethoscope 1025, a display 1030, an input component 1035, a controller 1040, a top cover 1060, and a bottom cover 1065.

The controller 1040 may include one or more of the bus 210, the processor 220, the memory 230, the storage component 240, and/or the communication interface 270, as described above in connection with FIG. 2.

Additionally, the diagnostic device 110 may include one or more additional sensors such as an electrocardiogram (EKG) sensor, a thermal camera, an infrared camera, a flow sensor, a spirometer, a humidity sensor, a movement sensor, a glucose monitor, an audio reverberation sensor, an ultrasonic sensor, or the like.

The diagnostic device 110 is configured as a compact, multi-feature, hand-held device that is configured to obtain diagnostic information by seamlessly imaging a user's ear, nose, and throat (ENT), and other superficial organs (e.g., skin, eyes, etc.), recording the user's breathing, heartbeat, and stomach and other body sounds, and measuring the user's body signals such as temperature, oxygen saturation and heart rate.

The diagnostic device 110 is configured to be controlled by the diagnostic application of the user device 120 that allows the user to securely build the user's profile, collect body signals on-demand, and conveniently maintain the user's health records in a single place.

The user may securely (and wirelessly) share the diagnostic information with the user's telehealth or primary care physician who, upon review, can provide a more data-centric diagnosis based on visual validation of clinical information, body signals, and user data.

The diagnostic device 110 is configured to implement artificial intelligence (AI) algorithms, and utilize advanced sensors and a test-reader functionality to allow at-home testing of common ailments (e.g., ENT infections, allergies, nutritional and other biomarkers, etc.).

The diagnostic device 110 is configured as a compact hand-held device that features multiple sensors configured to obtain diagnostic information by measuring physiological parameters. As an example, the diagnostic device 110 may include a seven inch length, a two inch width, and a one inch depth. It should be understood that myriad other dimensions are applicable. In this way, the diagnostic device 110 is both functionally and ergonomically efficient.

FIG. 3A shows the diagnostic device 110 laying down on one side, and shows the head of the diagnostic device 110 on the right end and the base of the diagnostic device 110 on the left end.

The temperature sensor 1020 is configured for no-contact user temperature measurements, and is provided on top of the diagnostic device 110 where the bulbous head plateaus (right side as shown in FIG. 3A). The diagnostic device 110 is held in close proximity to the skin and provides a body temperature readout. The temperature sensor 1020 sits in a recessed cavity under the shell, and is configured to maintain sufficient distance from the skin in order to generate more accurate and reproducible readouts. Additionally, the diagnostic device 110 may include ear or temporal artery (forehead) temperature sensors.

On one side of the bulbous device head sits a high-performance multi-focal endoscopic camera 1015 with zoom and color/light/gain ranging adjustments to capture images of the user's ENT, skin, eyes, and any other relevant organs. The camera 1015 may be a 640×480 pixel resolution camera (or a 1280×960 pixel resolution camera), may be about 3.9-5.5 mm in diameter, and may be configured to image objects that fall within a focal distance of 20-100 mm. In this way, all the intended body parts may be imaged at maximum (or improved) resolution. For example, when imaging the throat, the camera 1015 is held in proximity to the front of the mouth of the user, and the approximate distance from the camera lens to the back of the throat is about 80 mm. Similarly, when performing otoscopy to image ear structures for signs of infection or rupture detection, the camera focal distance is about 30 mm, which is within the performance specifications of the camera 125. It should be understood that myriad other dimensions and spatial relationships are possible.

The camera 1015 is connected via USB to the controller 1040 inside the diagnostic device 110. In order to perform optimum (or improved) imaging, the camera 1015 wirelessly streams (e.g., via Wi-Fi Direct, etc.) a live video feed to the diagnostic application on the user device 120. In this way, the user may visualize, in real time, what the camera 1015 captures. The user can use the video live stream on the diagnostic application to appropriately position the camera 1015 for an optimal (or improved) image and perform a touch input via the diagnostic device 110 (e.g., via the input component 1035) or the diagnostic application of the user device 120 to capture an image. In this way, the highest resolution and best position image for user and physician viewing may be obtained.

A digital stethoscope 1025 is provided on the opposing side of the head. The digital stethoscope 1025 includes a flat diaphragm that faces outward. The flat diaphragm is the only part of the stethoscope 135 that is visible to the user, and contacts the user's body for auscultation readings. Hidden behind the diaphragm, and internal to the diagnostic device 110 sits a metal casing containing a micro-electromechanical system (MEMS) or piezoelectric microphone 1020. The microphone 1020 is configured to record and amplify audio sounds, while filtering out higher frequency ambient noise to provide a high fidelity audio of a beating heart, breathing lungs, stomach sounds, or other internal body sounds. The analog signals are converted to digital via an analog-to-digital audio converter that interfaces with the controller 1040.

An integrated pulse oximeter 1010 and heart-rate monitor biosensor module are provided a few inches down the diagnostic device from the camera 1015. The integrated pulse oximeter 1010 and heart-rate monitor biosensor module include internal LEDs, photodetectors, optical elements, and low-noise electronics with ambient light rejection. The integrated pulse oximeter 1010 and heart-rate monitor biosensor module is configured to operate on very low power, and offer a fast-data output capability and high signal to noise ratio. The user simply places the user's thumb or finger over the integrated pulse oximeter 1010 and records their oxygen-saturation and heart rate/pulse. The pulse oximeter 1010 may be configured as a grip. In this case, the user places the user's thumb over the embedded sensor and holds the user's thumb on the sensor for a threshold timeframe. In this way, the diagnostic device 110 may obtain an oxygen saturation, a heart rate, and a pulse of the user.

A display 1030 is provided across from the integrated pulse oximeter 1010, and is configured to display the user's measurements, such as body signals (e.g., temperature, oxygen saturation, heart rate, respiration rate, etc.) on the diagnostic device 110. The display 1030 permits the user to visualize the user's body signals without requiring that the diagnostic device 110 interface with the user device 120. Further, the display 1030 provides the user with a status reading of the device power and other readouts.

The diagnostic device 110 includes operational input component 1035 under the display 1030 to control the diagnostic device 110 (e.g., turn the diagnostic device 100 on and off), record images from the camera 1015 or audio sounds from the stethoscope 1025. A power-status indicator using LEDs informs the user on the battery level. The diagnostic device 110 is controlled by a battery 1005 that powers the diagnostic device 110.

The sensors on the diagnostic device 110 are controlled via the controller 1040 that is configured to allow for the libraries of the various sensors to be used. The controller 1040 features Wi-Fi and inter-integrated circuit ($I^2c$) communication capabilities. The controller 1040 has microphone pads (e.g., ADC onboard for the stethoscope 1025) and an audio out feature (e.g., a headphone jack). The controller 1040 features a USB for storage access and charging of the onboard battery 1005. The controller 1040 is configured to stream a live video feed and interfaces with the display 1030. The controller 1040 is configured to operate as an onboard computer, and allows interfacing the diagnostic device 110 with a software application installed on the user device 120 (e.g., the diagnostic application). The controller 1040 and the application connect wirelessly (e.g., via Bluetooth or Wi-Fi) and allow device control, and fast data transfer rates of diagnostic information such as body signal measurements, audio recordings, and images (e.g., still photos and video).

The diagnostic device 110 may include a thermal/far infrared camera configured to measure changes in the temperature of different parts of the body, and detect areas of pain or inflammation. Further, the diagnostic device 110 may include an EKG sensor on the handle to detect heart rhythm, and to identify abnormal heart rhythms. Further, the diagnostic device 110 may include a peak flow monitor and spirometer configured to determine airflow levels in users with chronic obstructive lung disease like asthma and chronic obstructive pulmonary disease (COPD). Further, the diagnostic device 110 may include sensors (e.g., temperature, humidity, movement, etc.) configured to detect breathing patterns and respiratory rate. Further, the diagnostic device 110 may include sensors configured to detect fluid behind eardrum utilizing audio reverberations The diagnostic device 110 may include an attachment area to connect a wrist or arm blood pressure cuff. Further, the diagnostic device 110 may include attachments to other smart devices including glucometers, scales, blood pressure cuffs, patches for cuffless blood pressure testing, etc.

The diagnostic device 110 may include a transducer module that is configured to sends inaudible high-frequency sound waves into the body, and detect returning echoes. Most ultrasound devices and platforms are primarily utilized by specialists in physician offices. In remote areas or on the battlefield, the ability to acquire, reconstruct, and wirelessly stream images to a telehealth physician, providing at least some data-rich information, offers a valuable pre-consultation and serves as a precursor to an in-person physician visit. The diagnostic device 110 may provide a preliminary assessment of clinical information such as ligament sprains, strains, tendon or muscle tears, fluid collections in inflammatory settings, hernias, hip dislocations, or fluid in hip joints in children.

Using nano-diagnostics, imaging, and sensing technologies, the diagnostic device 110 is configured to utilize point-of-care and at-home test kits. For example, the diagnostic device 110 may be configured to utilize single-use chips/wafers pre-loaded with gold or different material-based nanoparticles that can bind to infectious agents (e.g., viruses, bacteria, fungi, parasites, etc.), body fluids, or hormones (e.g., hCG pregnancy test) and offer fluorescent and/or colorimetric readouts.

The chips may be provided in a ready-to-use housing chamber and contain instructions for the user to add the user's body fluid sample (e.g., urine, saliva etc.) and follow a test protocol. The top lid of the housing chamber includes a small puncturing pin. The chamber may be initially sealed to prevent contamination and tampering. The chamber comes preloaded with a nano-diagnostic wafer, underneath which sits a dissolvable reagent packet containing a test solution.

The user may open the sealed housing chamber, remove the wafer, and take out the reagent packet underneath the wafer. After the user adds the user's body fluid sample to the wafer, the user adds the components back to the chamber in reverse order. The user first places the wafer, and then places the reagent packet on top of the wafer. After the user closes the lid, the reagent packet gets punctured and the test solution reacts with the wafer nanoparticles for a specified reaction time (e.g., ranging from ten minutes to a few hours).

Following this "detection reaction," the housing chamber bottom lid is opened to allow any extra solution to drain out. The chip is then removed and inserted into the diagnostic device 110 via a diagnosis tray similar to inserting a SIM card on a smartphone SIM card tray.

A detector on the diagnostic device 110 reads out the sample and provides a diagnosis. Data readouts are transmitted to the diagnostic application of the user device 120 or to the platform 130 for physician review.

Alternatively, the user orders a specific diagnostic wafer (e.g., a strep throat wafer, a UTI wafer, etc.) that comes in a small plastic cup-like packet that also contains a powdered or lyophilized reagent sealed with a piece of foil. The wafer is the bottom of the cup-like design and open to the outside (e.g., not enclosed with plastic). The wafer contains a cotton-like absorbent material. Utilizing a dropper, the user can put 3-4 drops of the relevant body fluid on the bottom of the cup/wafer. The cup is then placed in the diagnostic device 110. When a button is pushed, the diagnostic device 110 pierces the foil seal at the top of the cup, and a couple drops of water/solution are added to the top of the wafer and combine with the lyophilized reagent to become active. The test solution reacts with the wafer nanoparticles for a specified reaction time (ranging from ten minutes to a few hours). The bottom of the diagnostic device 110 contains a light and/or light sensor that will read and interpret the nanoparticle reaction. The display 1030 displays the results.

Alternatively, a lyophilized reagent solution is embedded in the absorbent wafer. The user is instructed to put a couple drops of body fluid on the wafer. The body fluid liquid itself (e.g., urine or saliva) will combine with the embedded reagent to make it active. Alternatively, the user might be instructed to combine the user's body fluid sample with a sterile/saline solution first, and then place 3-4 drops on the wafer before placing it in the tray of the diagnostic device 110. For example, in cases like strep throat, where samples need to be obtained in the back of the throat, the user will swab the back of their throat with a cotton swab. The user may put a few drops of a sterile liquid or reagent solution in a small plastic tube, then place the cotton swab that contains a sample from the back of the throat in the tube and leave for a specified time. The user will then take a dropper to transfer 3-4 drops of the solution to the wafer that is then placed in the tray of the diagnostic device 110. The test solution reacts with the wafer nanoparticles for a specified reaction time (e.g., ranging from ten minutes to a few hours). The bottom of the diagnostic device 110 includes a light and/or light sensor that will read and interpret the nanoparticle reaction. The display 1030 displays the results. The diagnostic application of the user device 120 may also display the results for each wafer.

In this way, the diagnostic device 110 can provide accurate and reliable predictions without the need for users to drive to a lab for a follow-up swab test, which creates significant cost and time efficiencies. Utilizing these advanced features, point-of-care testing, and data-centric guidance, the diagnostic device 110 is a powerful AI-diagnostic tool that assists physicians in their telehealth diagnoses and disease management, and assists users to remotely manage their health.

FIGS. 4A-4E are diagrams of a user interface of a diagnostic application according to an embodiment. A user may interact with the user device 120 to cause the user device 120 to execute the client-version of the diagnostic application. For example, the user may interact with the diagnostic application via the user device 120 when the user has an ailment to be diagnosed, when the user intends to use the user device 120 to communicate the user's clinical information to a telehealth or primary care physician, when the user desires to obtain diagnostic information, etc.

Figure 4A:
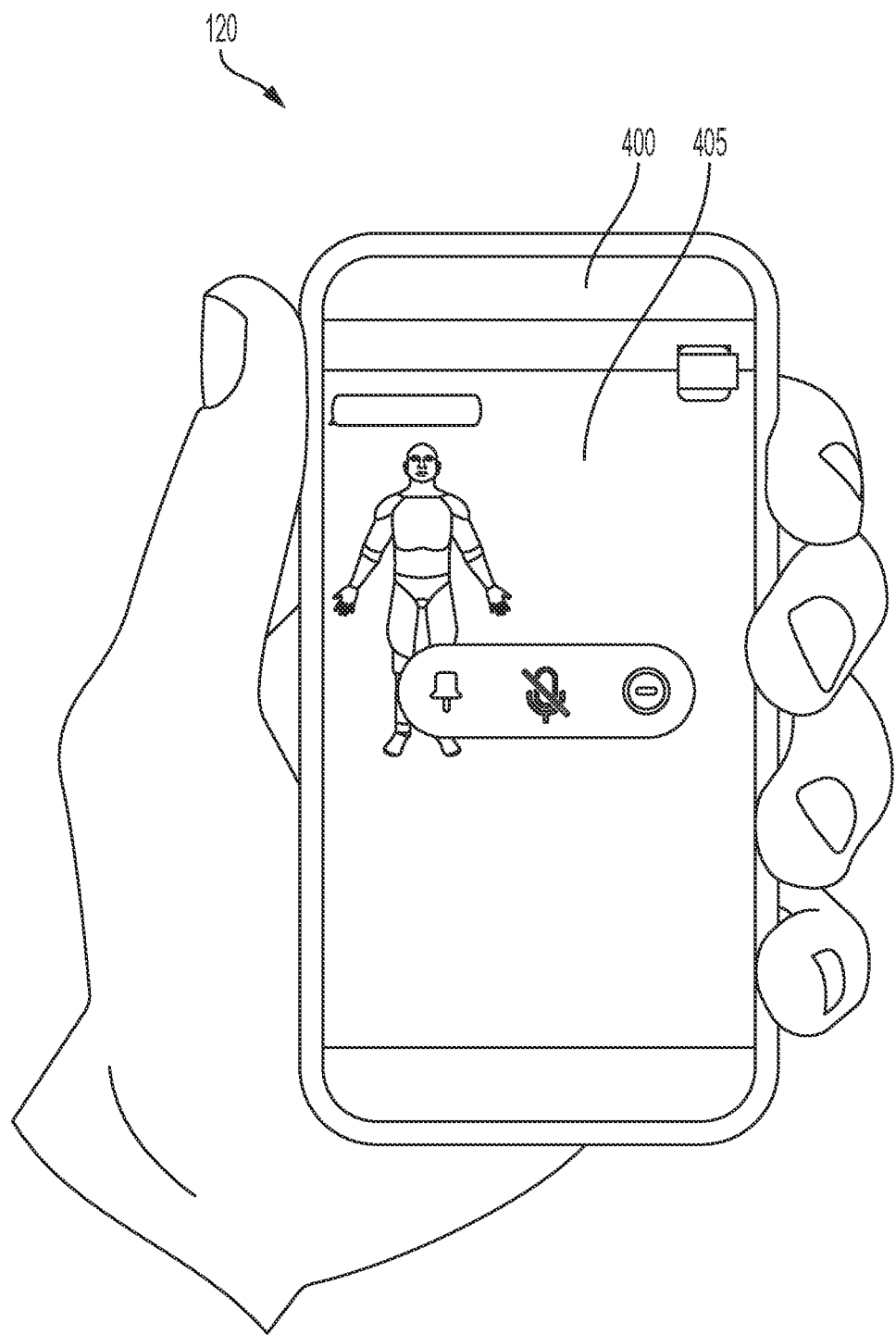
FIGS. 4A-4E are diagrams of a user interface of a diagnostic application according to an embodiment.

As shown in FIG. 4A, the user device 120 may display a user interface 400 for inputting diagnostic information. For example, the user device 120 may display the user interface 400 based on the user selecting to input diagnostic information to be used in determining a clinical assessment. As shown, the user interface 400 includes a body map image 405. The body map image 405 represents a body of the user, and segments the body of the user into discrete regions (e.g., a head region, a chest region, a shoulder region, a leg region, etc.).

Figure 4B:
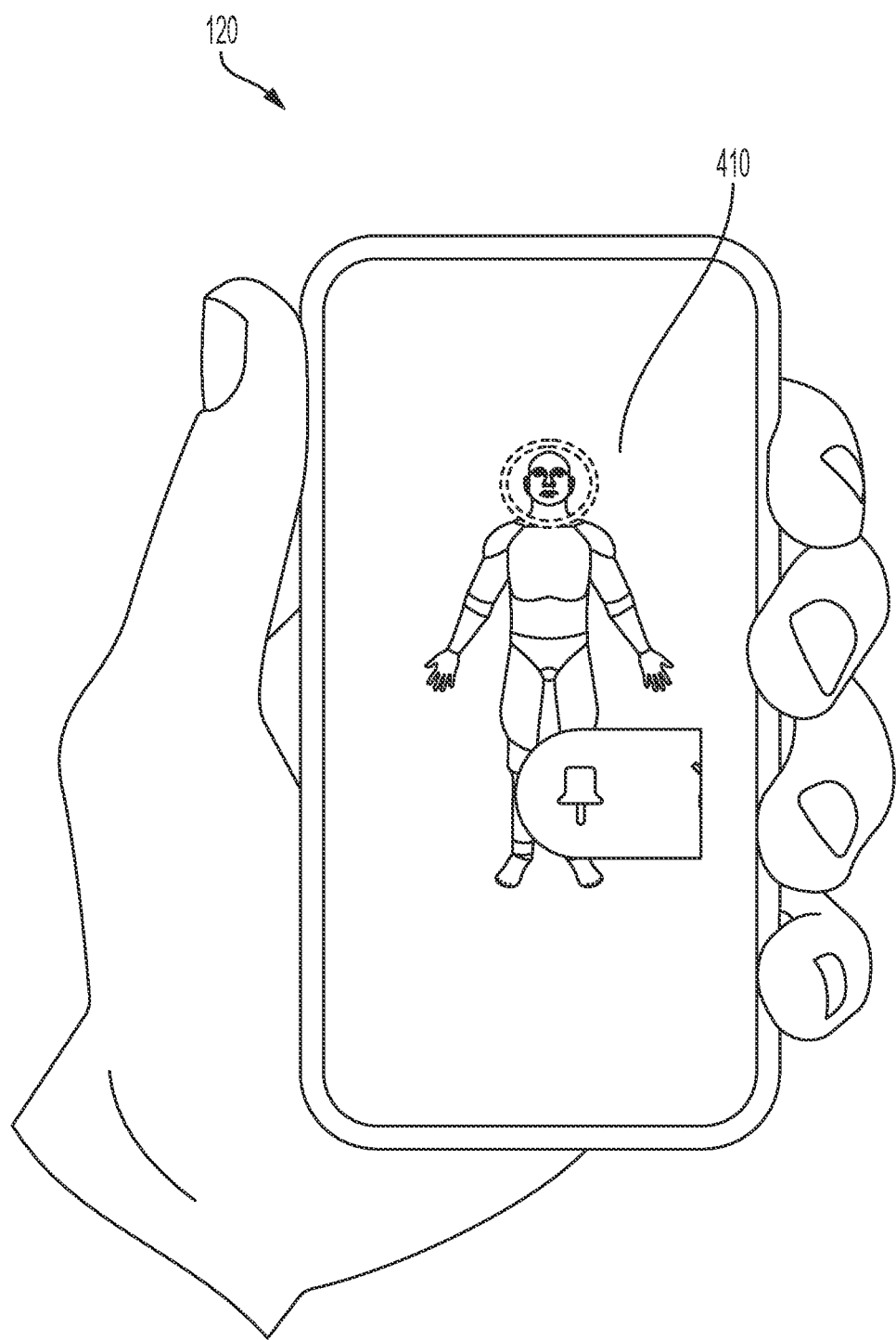

As shown in FIG. 4B, the user device 120 may receive an input 410 via the user interface 400 that selects a region of the body map image 405. For example, a user may perform a touch gesture in association with the body map image 405 to select a particular region. As an example, and as shown in FIG. 4B, the user may perform a touch gesture to select a region (a head region) of the body map image 405. As an alternative, the user may use a pull-down menu to select a body region.

Figure 4C:
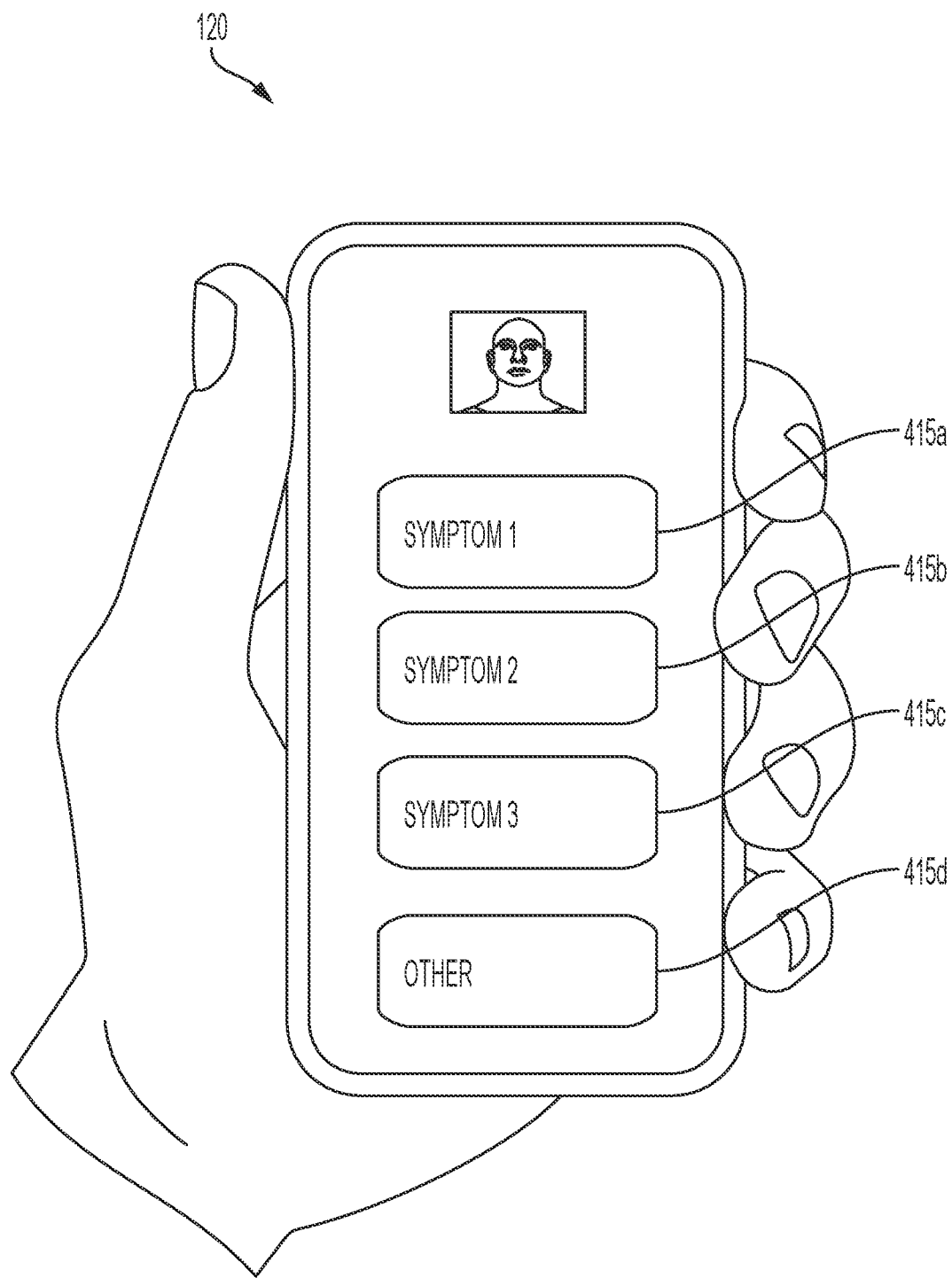

As shown in FIG. 4C, the user device 120 may display a set of user interface elements 415a-415d that correspond to particular clinical information associated with the region selected by the user. The user device 120 may display clinical information associated with the region. For example, the user device 120 may display the n most common clinical information associated with the region 410. Additionally, the user device 120 may display a user interface element 415d corresponding to "other" that permits the user to manually input clinical information, or to select particular clinical information from a list of clinical information.

Figure 4D:
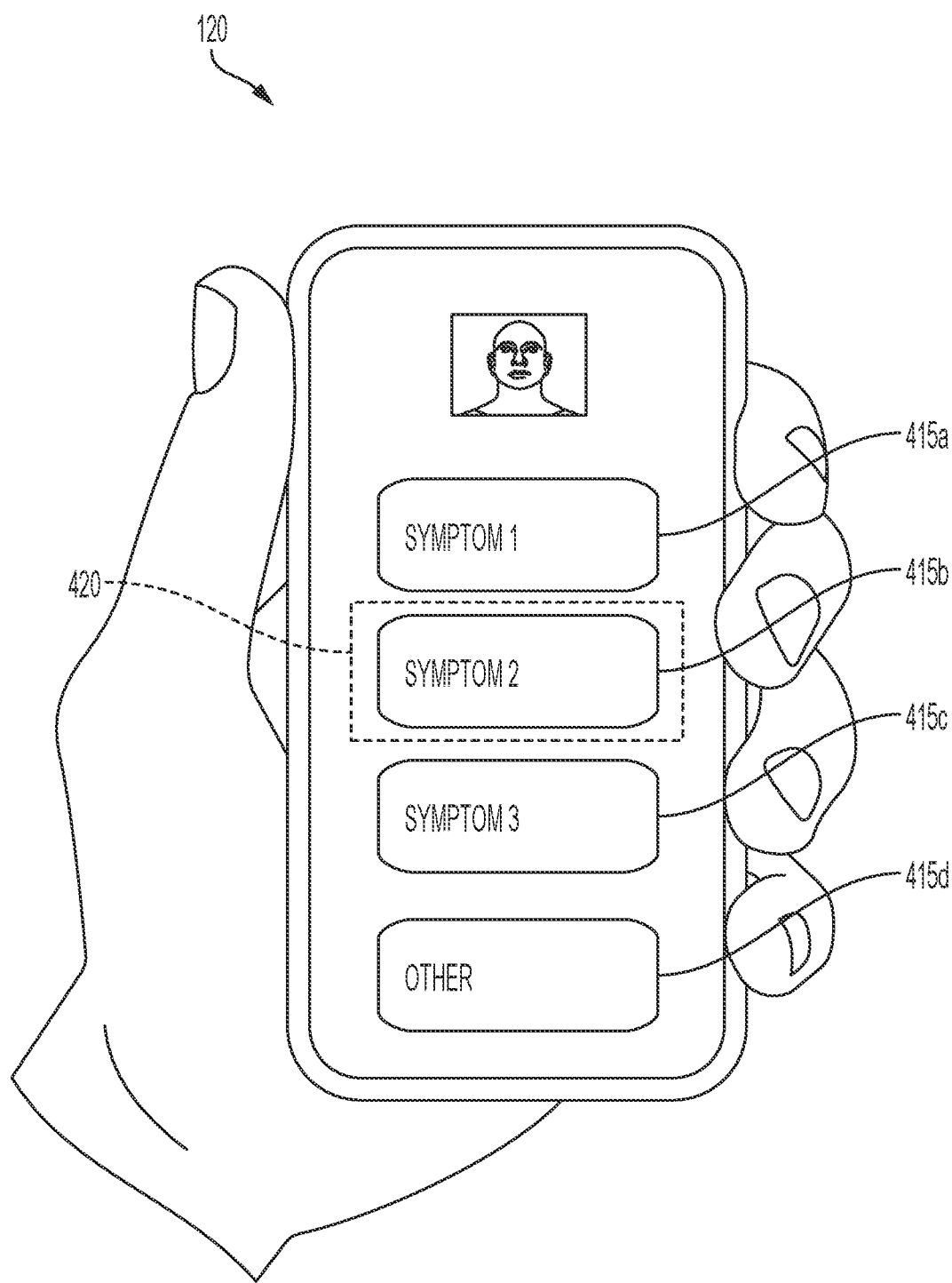

As shown in FIG. 4D, the user device 120 may receive an input 420 via the user interface 400 that selects a user interface element 415. For example, the user may perform a touch gesture in association with the user interface element 415*b*, and the user device 120 may receive the input 420 that identifies particular clinical information.

Figure 4E:
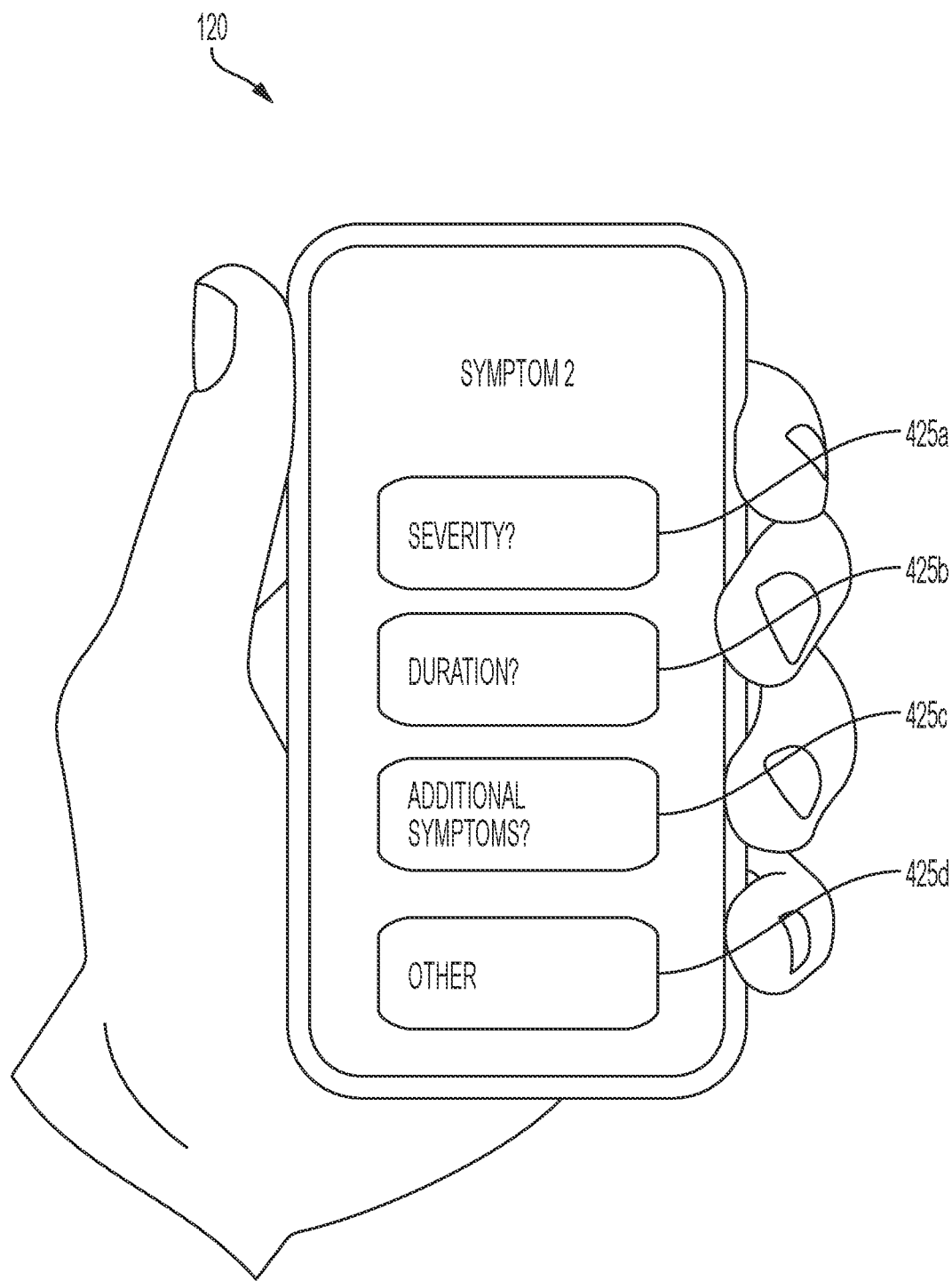

As shown in FIG. 4E, the user device 120 may display a set of user interface elements 425*a*-425*d* that correspond to particular prompts associated with the clinical information selected by the user. Based on a selection of a user interface element 425 corresponding to a prompt, the user device 120 may display additional information associated with the prompt that permits a user to respond to the prompt. For example, the prompts may include a severity prompt with additional information identifying "severe," "moderate," "mild," etc., a duration prompt with additional information identifying "better," "worse," "same," etc., an additional clinical information prompt with additional information identifying additional clinical information, and an "other" prompt that permits the user to input information associated with the clinical information. In this way, the user may input various diagnostic information via the user interface 400 of the user device 120 that identifies a potential ailment of the user, a location of the ailment, clinical information of the ailment, severity of the ailment, etc.

FIGS. 5A-5G are diagrams of a user interface of the diagnostic application according to an embodiment.

As shown in FIG. 5A, the user device 120 may display a user interface 500 for obtaining diagnostic information from the diagnostic device 110. For example, as shown, the user device 120 may display a set of user interface elements 505*a*-505*d* that correspond to diagnostic information (e.g., temperature, oxygen saturation, audio, images, etc.) that can be obtained by respective components of the diagnostic device 110. In some cases, the user device 120 may display suggested diagnostic information to be obtained, based on the input diagnostic information (e.g., clinical information), based on previous usage of the diagnostic device 110, based on a user configuration of the diagnostic device 110, or the like.

Figure 5B:
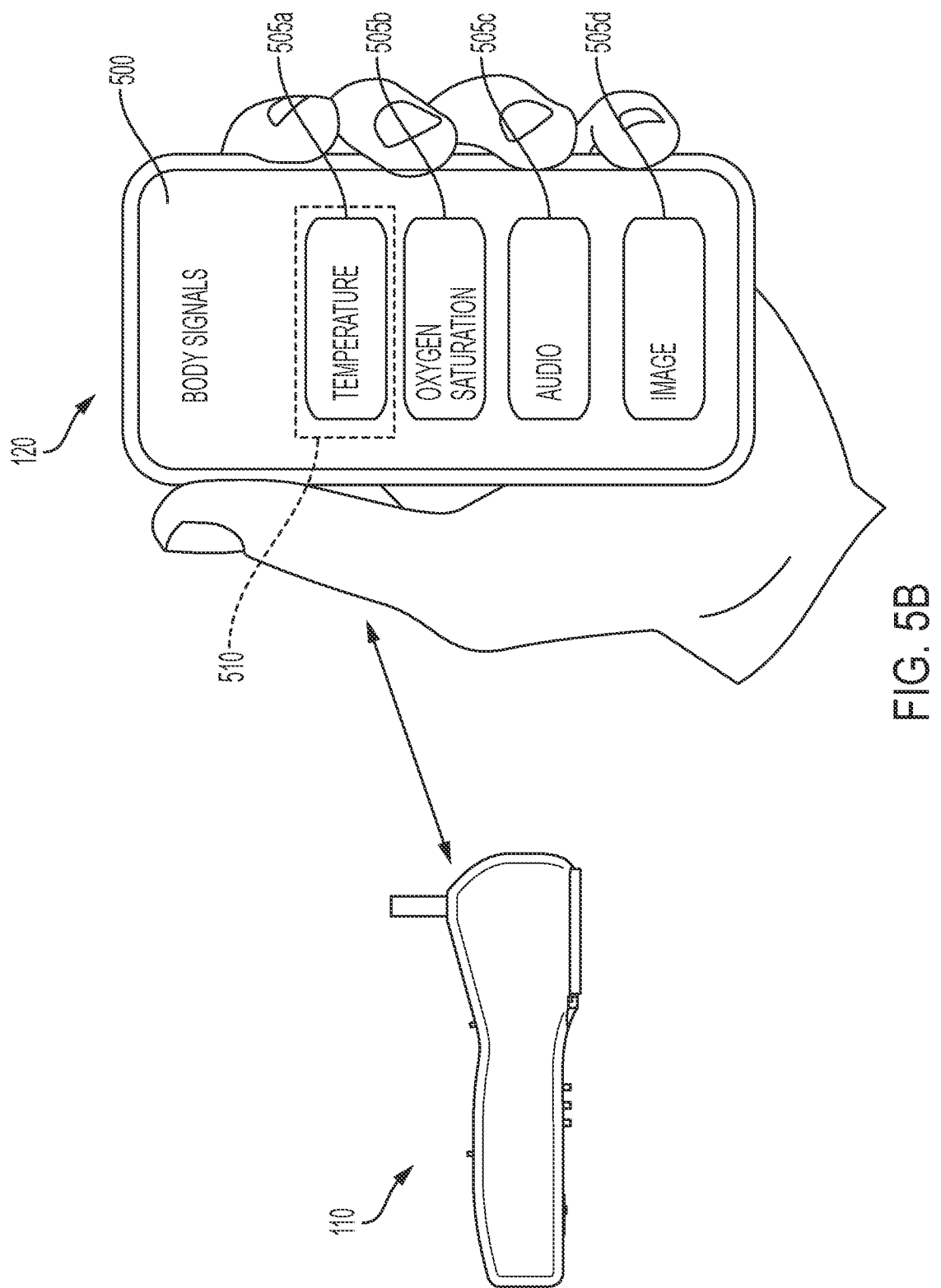

As shown in FIG. 5B, the user device 120 may receive an input 510 via the user interface 500 that selects a user interface element 505*a*. For example, the user may perform a touch gesture in association with the user interface element 505*a*, and the user device 120 may receive the input 510 that identifies particular diagnostic information to be obtained (i.e., temperature).

Figure 5C:
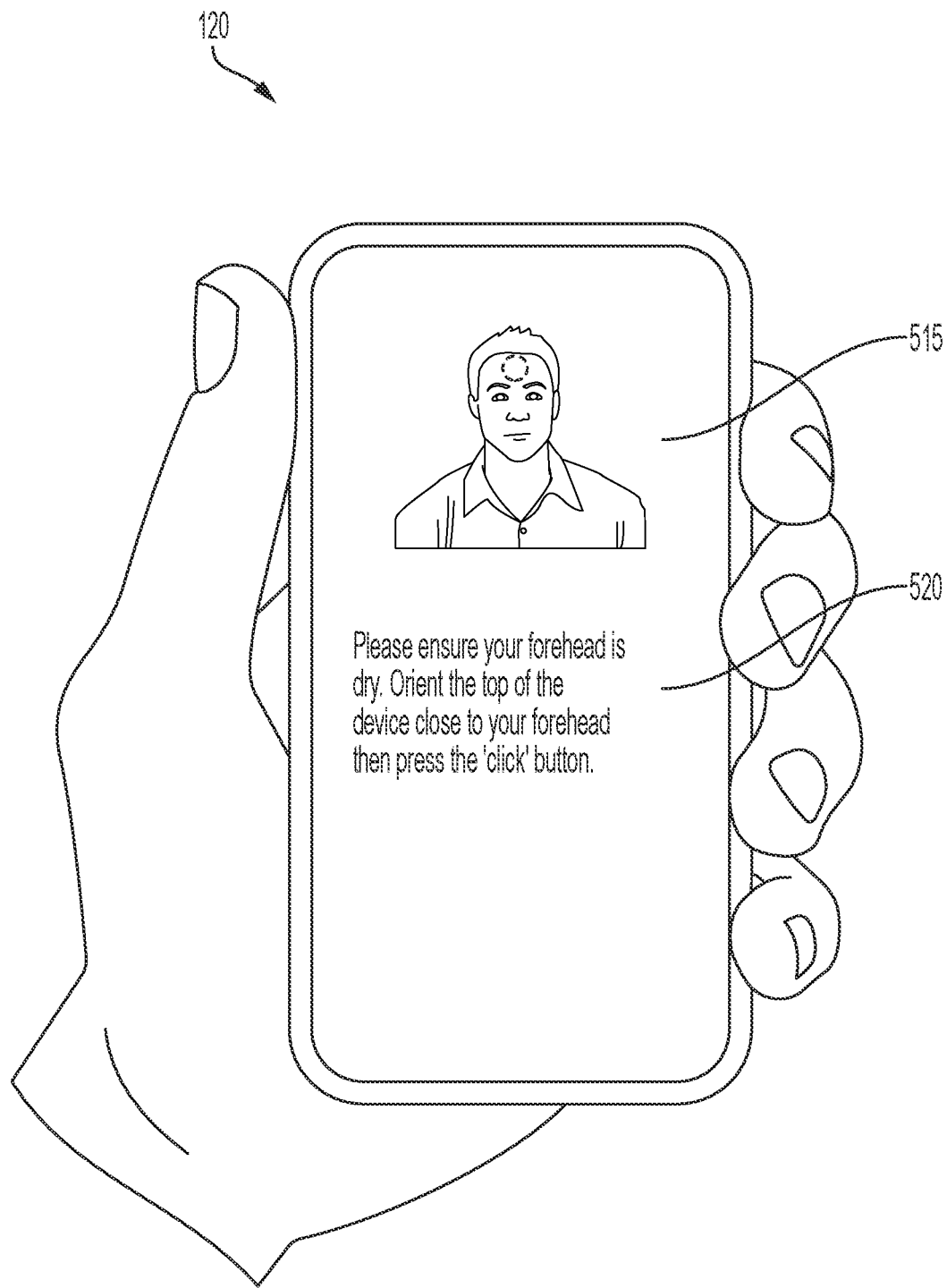

As shown in FIG. 5C, the user device 120 may display body location information 515 that identifies a location of the body at which the diagnostic device 110 should be placed in order to obtain the selected diagnostic information. For example, as shown, the body location information 515 includes an image of a head and an indicator identifying a location on the head at which the diagnostic device 110 should be placed in order to obtain the user's temperature. As further shown in FIG. 5C, the user device 120 may display instructions 520 regarding preparation and placement of the diagnostic device 110. The user may interact with the diagnostic device 110 in order to cause the diagnostic device 110 to obtain the diagnostic information. Further, the diagnostic device 110 may provide the diagnostic information to the user device 120 based on obtaining the diagnostic information.

As shown in FIG. 5D, the user device 120 may update the display of the set of user interface elements 505*a*-505*d*, based on obtaining the selected diagnostic information. For example, after the user device 120 receives the diagnostic information (i.e., temperature) from the diagnostic device 110, the user device 120 may update a user interface element 505*a* associated with the diagnostic information to identify that the diagnostic information has been successfully obtained.

Figure 5E:
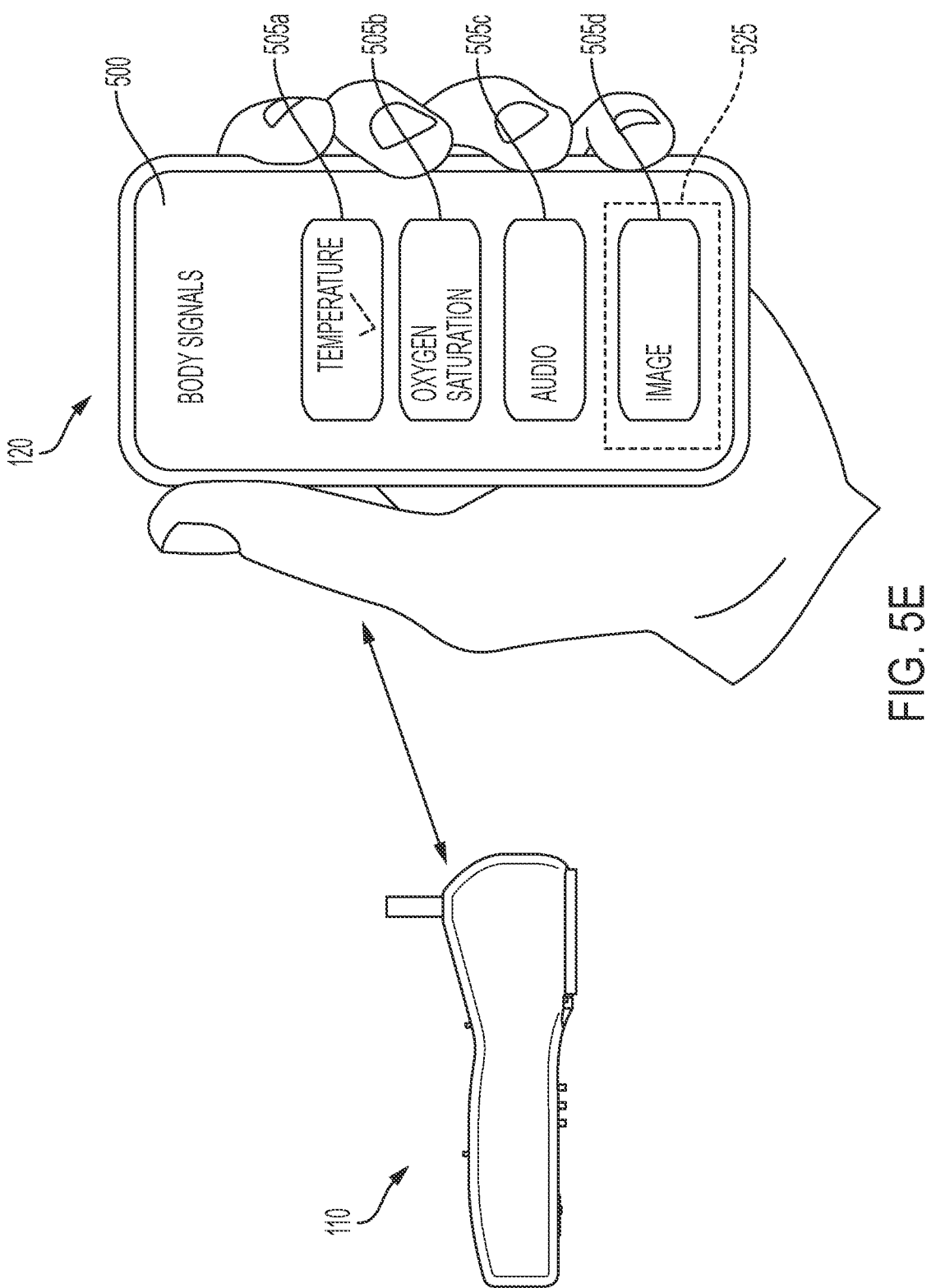

As shown in FIG. 5E, the user device 120 may receive an input 525 via the user interface 500 that selects another user interface element 505*d*. For example, the user may perform a touch gesture in association with the user interface element 505*d*, and the user device 120 may receive the input 525 that identifies particular diagnostic information to be obtained (i.e., image information).

Figure 5F:
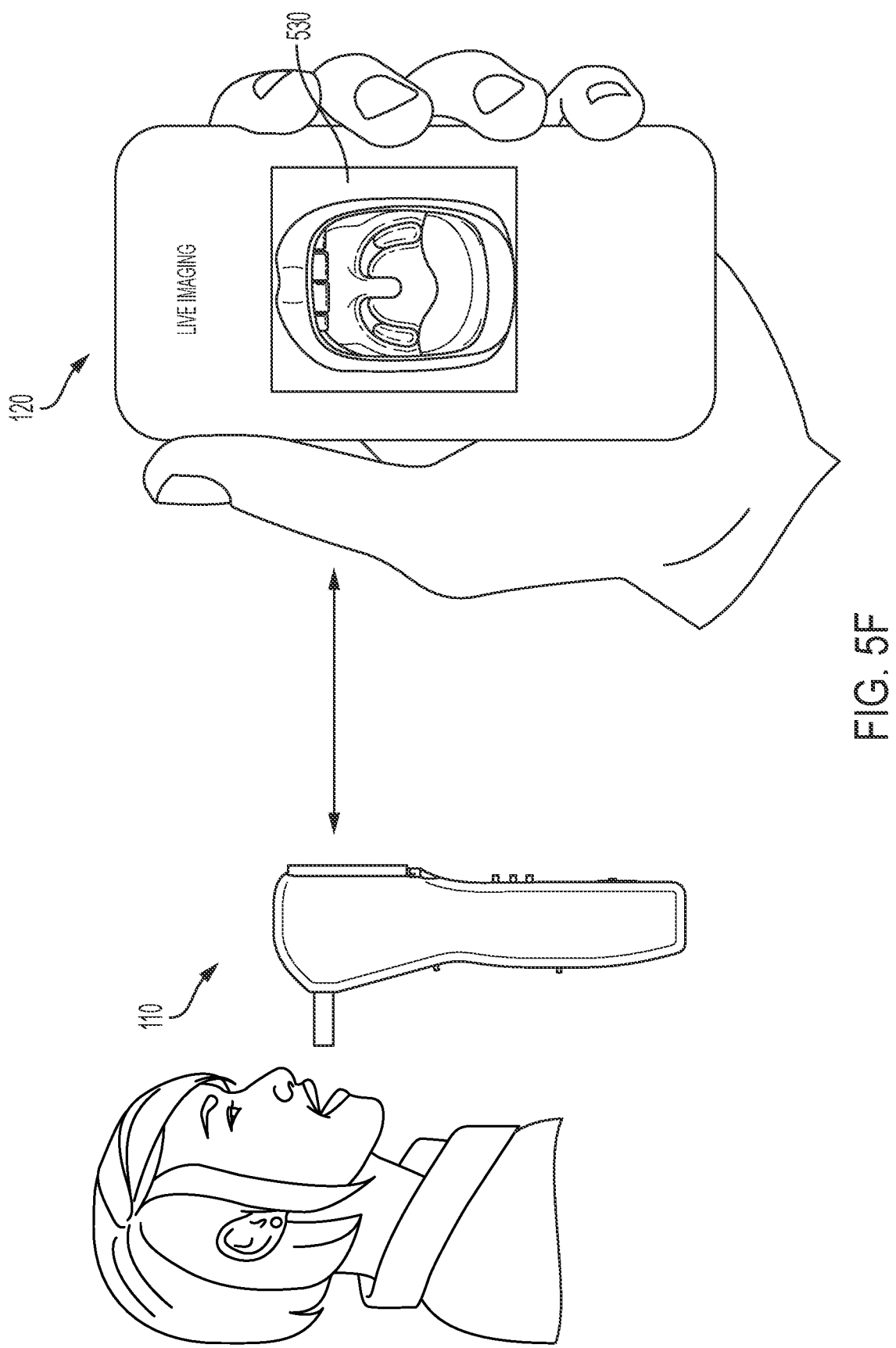

As shown in FIG. 5F, the user device 120 may display video information 530 obtained from the diagnostic device 110. For example, as shown, the user may place a camera 1015 (or the camera 1060) of the diagnostic device 110 in proximity to the user's throat, and the diagnostic device 110 may obtain video information of the user's throat. Further, the diagnostic device 110 may provide the video information to the user device 120. Further still, the user device 120 may concurrently display the video information 530 via the user interface 500. In this way, the user may view the video information 530 as the user obtains video information of a body part, which permits the user to intuitively identify whether the placement and positioning of the diagnostic device 110 is satisfactory.

The user device 120 may display device position information that identifies a placement of the diagnostic device 110 with respect to the body of the user. Additionally, the user device 120 may display device position information that identifies a target position of the diagnostic device 110 with respect to the body of the user. Additionally, the user device 120 may display device position information that identifies a current position of the diagnostic device 110 and the target position of the diagnostic device 110, and that provides an indication on how to move the diagnostic device 110 to the target position. For example, the user device 120 may display a suggested movement path from the current position to the target position, may display an instruction regarding a suggested movement path (e.g., "move the diagnostic device upwards"), may output an audible instruction, may output audible beeps or visual LED blinks that identify whether the current position can be improved, etc.

Figure 5G:
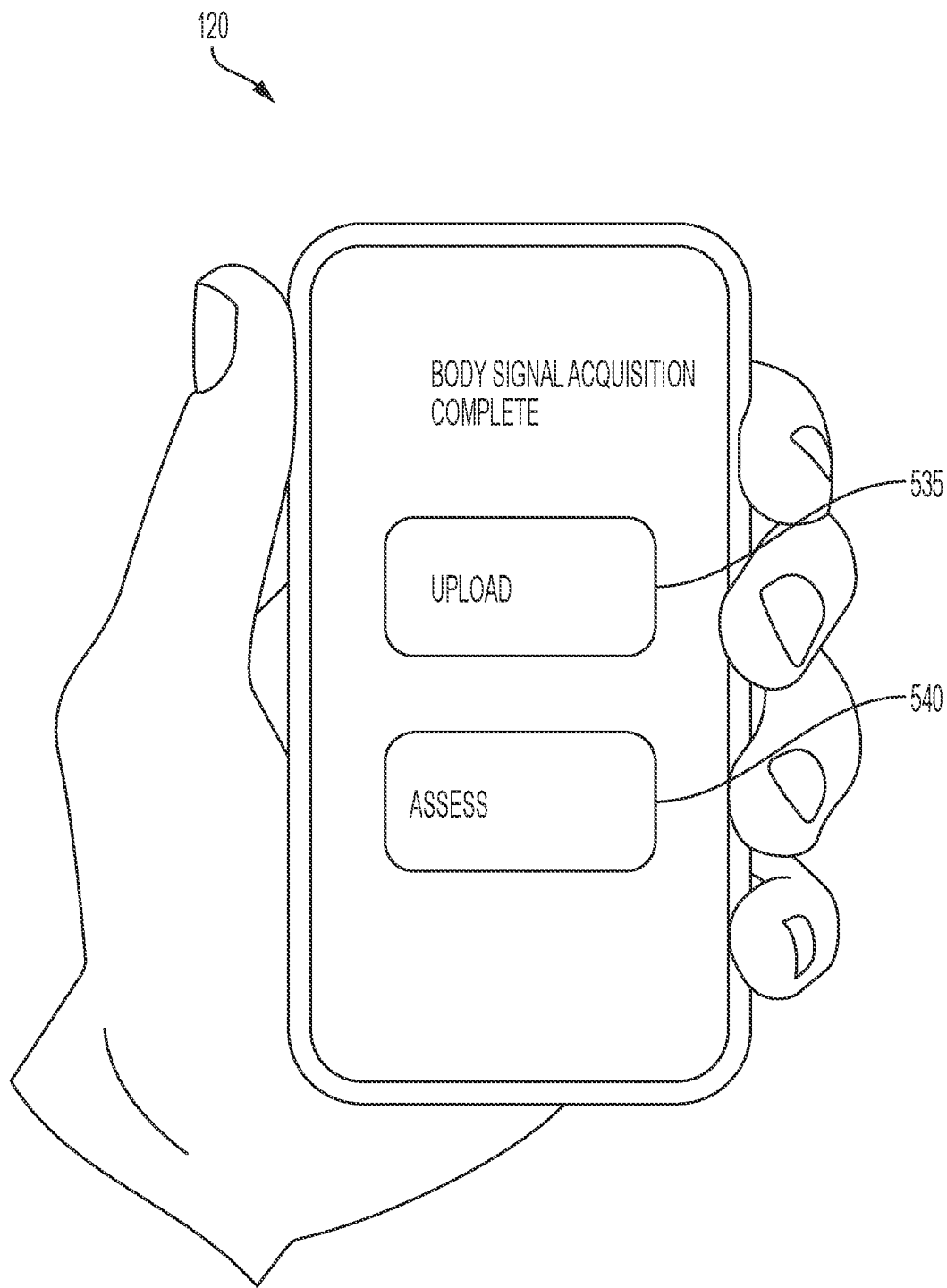

As shown in FIG. 5G, the user device 120 may display a user interface element 535 that permits the user to select that the obtained diagnostic information be uploaded to the platform 130. Additionally, as shown in FIG. 5G, the user device 120 may display a user interface element 540 that permits the user to select that a diagnosis be determined based on the obtained diagnostic information. The user device 120 may display the user interface elements 535 and 540 based on obtaining the diagnostic information from the diagnostic device 110. For example, the user may desire to obtain a certain amount of desired diagnostic information, and may use the diagnostic device 110 to obtain the particular diagnostic information. After obtaining the diagnostic information, the user can select whether to send the diagnostic information to a medical professional (as shown in FIGS. 6A-6E), or whether to have an AI model determine a diagnosis (as shown in FIGS. 7A-7C).

FIGS. 6A-6E are diagrams of user interfaces of the diagnostic application according to an embodiment.

Figure 6A:
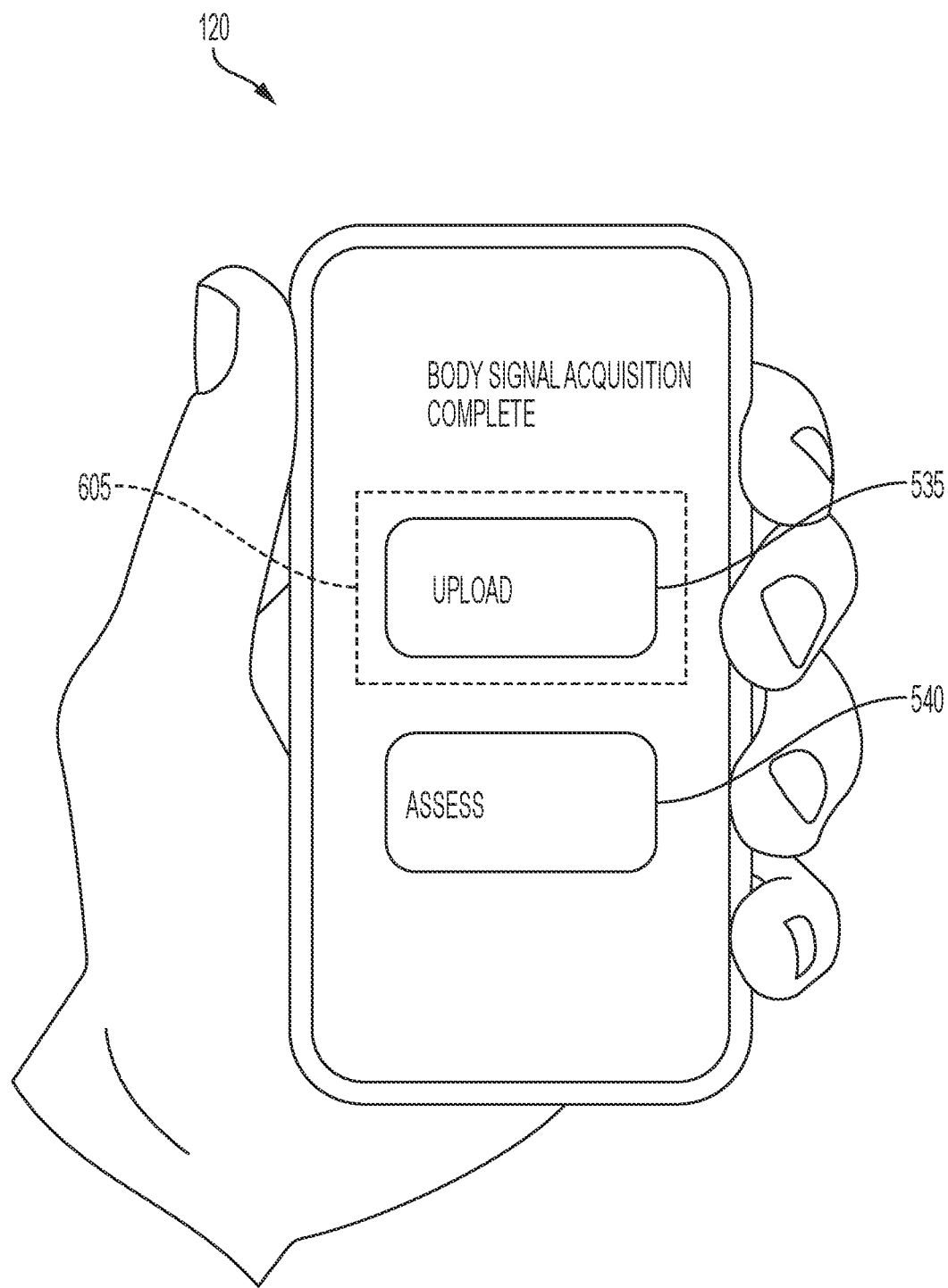
FIGS. 6A-6E are diagrams of user interfaces of the diagnostic application according to an embodiment.
Figure 7A:
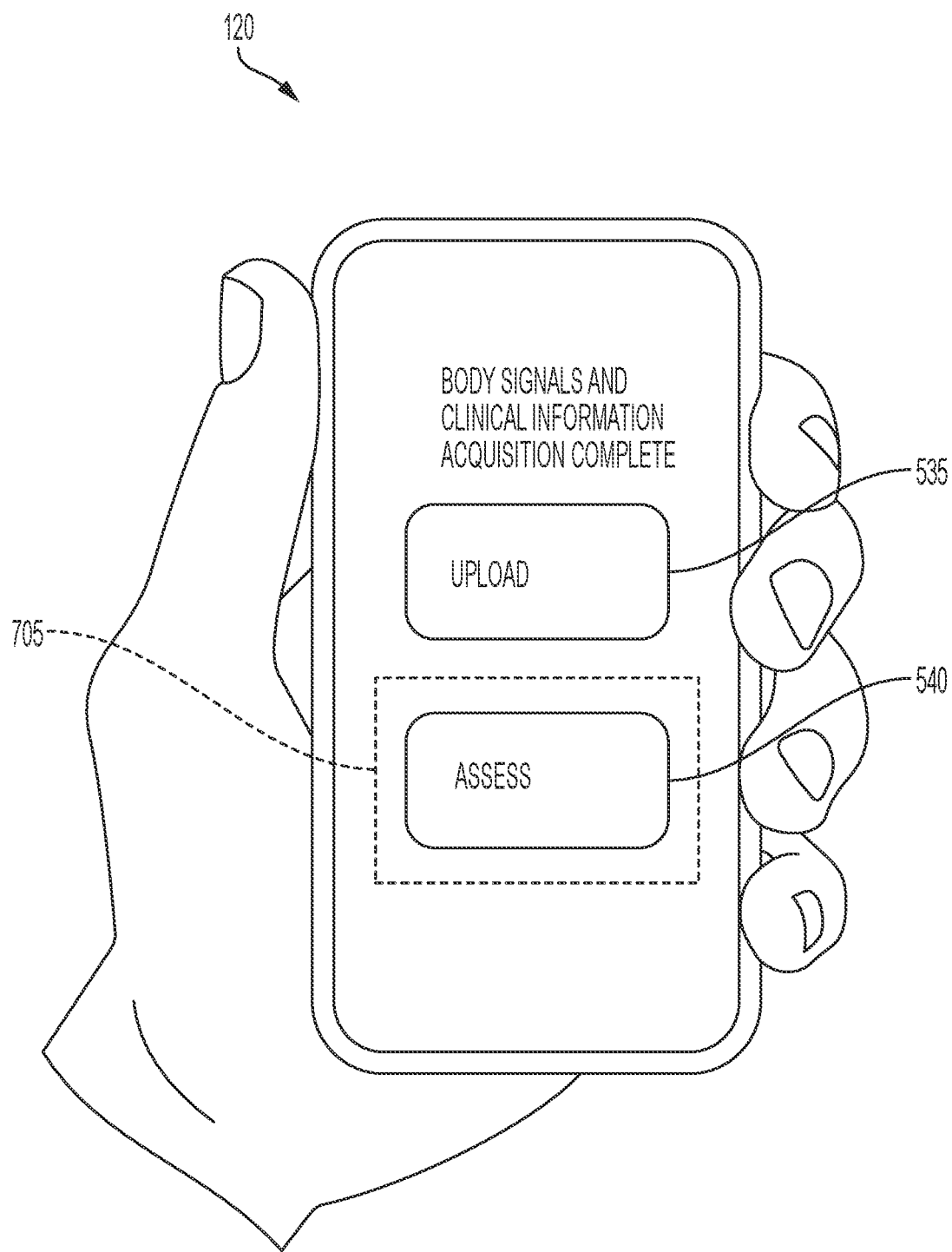
Figure 7C:
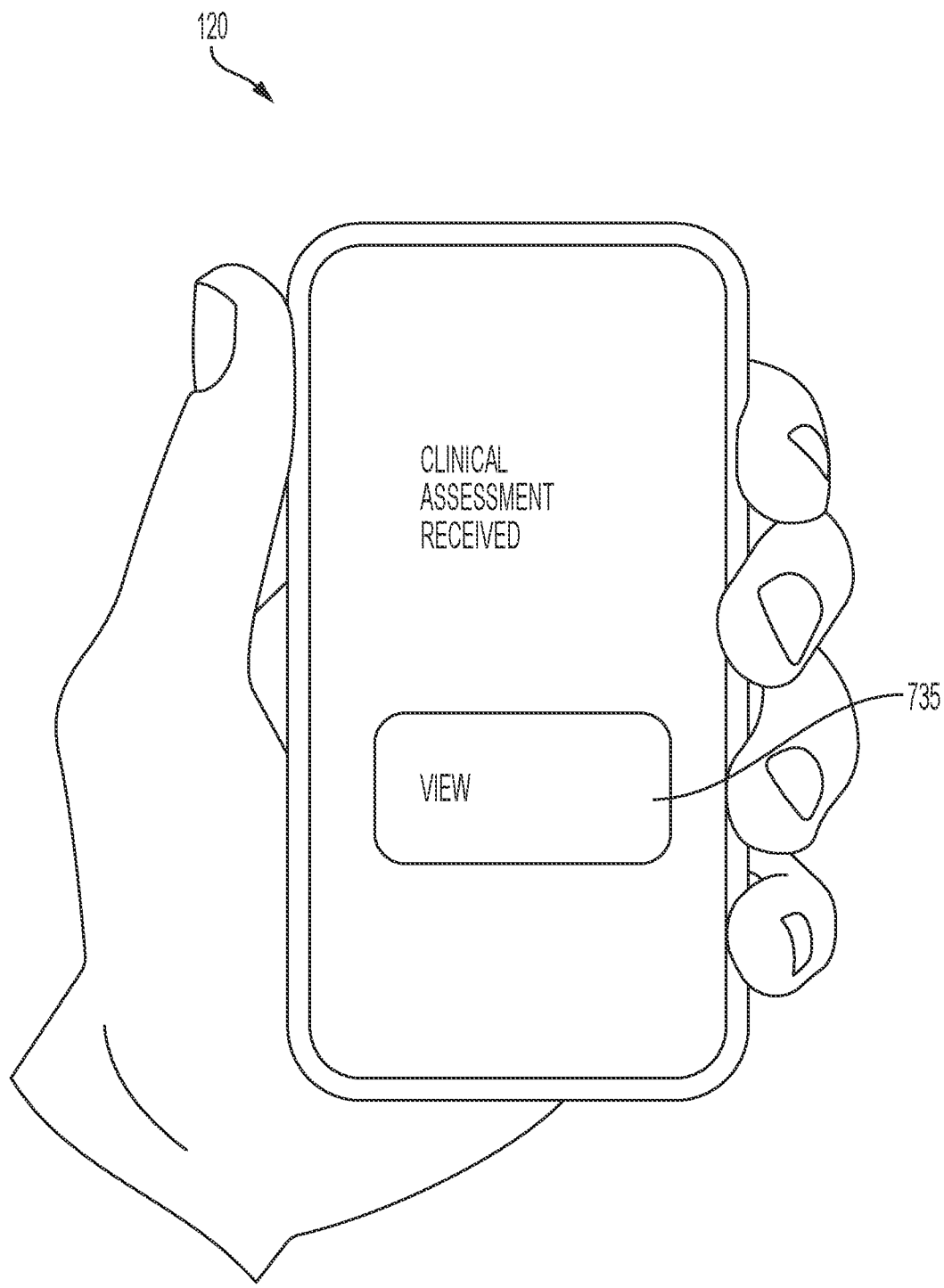

As shown in FIG. 6A, the user device 120 may receive an input 605 via the user interface 500 that selects a user interface element 535 that identifies that the obtained diagnostic information is to be uploaded to the platform 130. For example, the user may perform a touch gesture in association with the user interface element 535, and the user device 120 may receive the input 605 that identifies that the obtained diagnostic information is to be uploaded to the platform 130.

Based on the input 605, the user device 120 may provide the diagnostic information to the platform 130. The platform 130 may receive the diagnostic information, and store the diagnostic information. For example, the platform 130 may store the diagnostic information in HIPAA-compliant and subjective objective assessment plan (SOAP) formats. The user device 120 and the platform 130 may utilize cryptographic techniques to improve security of the diagnostic information. For example, the user device 120 and the platform 130 (and other peers) may utilize a blockchain to store the diagnostic information.

Based on providing the diagnostic information to the platform 130, the user device 120 may display a prompt indicating whether the user would like to allow a doctor to access the diagnostic information.

Figure 6B:
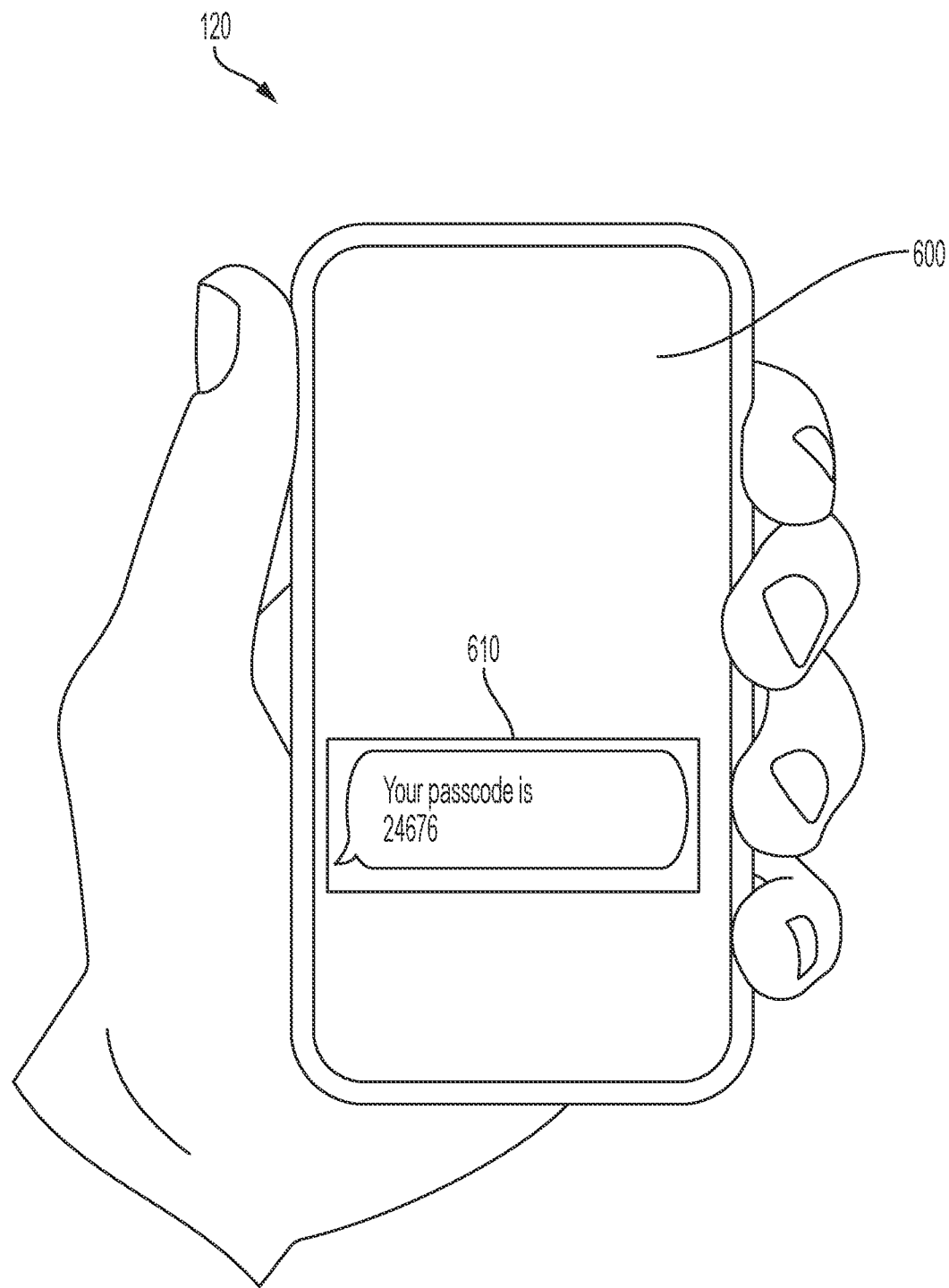

As shown in FIG. 6B, the user device 120 may display a short code (e.g., "24676"). For example, the user device 120 may receive a short code, such as one-time pass, from the platform 130 based on a user input identifying that the diagnostic information is to be shared with a doctor, and may display the short code. The user device 120 may receive the short code via a text messaging application, email, the diagnostic application, a telephone call, or the like.

The user may communicate the short code with the doctor with whom the user wishes to share the diagnostic information. For example, the user may communicate with the short code via a text messaging application, email, the diagnostic application, a telephone call, or the like.

Figure 6C:
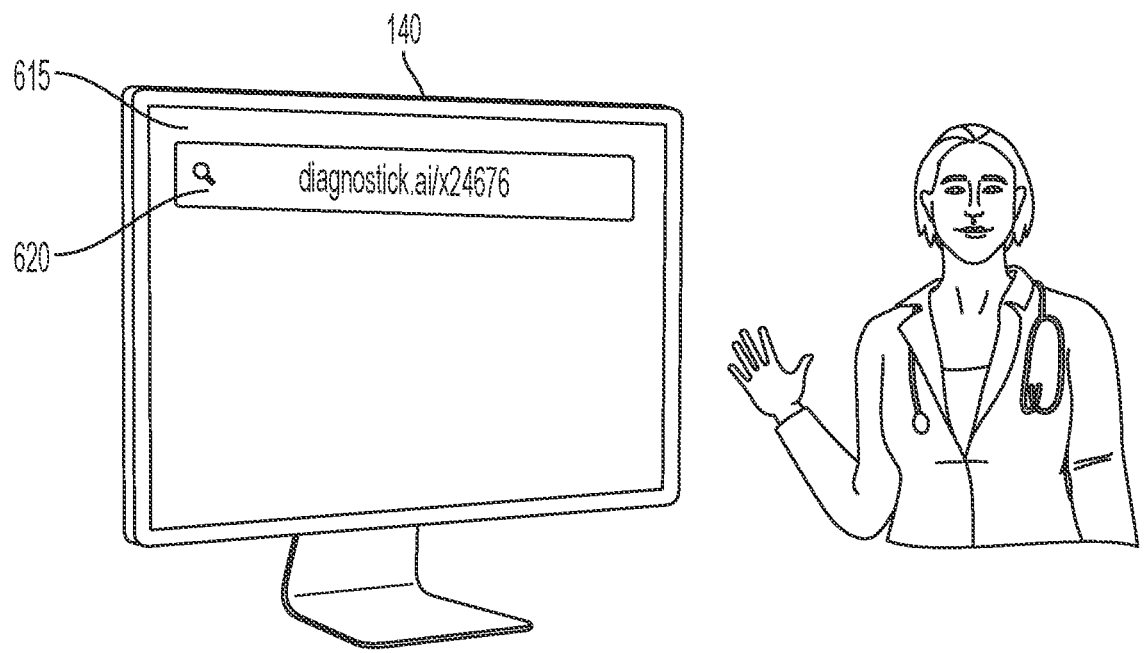

As shown in FIG. 6C, a doctor may use the short code to obtain access to the diagnostic information via the user device 140. For example, as shown, the doctor may input the short code as part of a uniform resource locator (URL). As other examples, the doctor may input the short code via the diagnostic application, via email, etc.

Figure 6D:
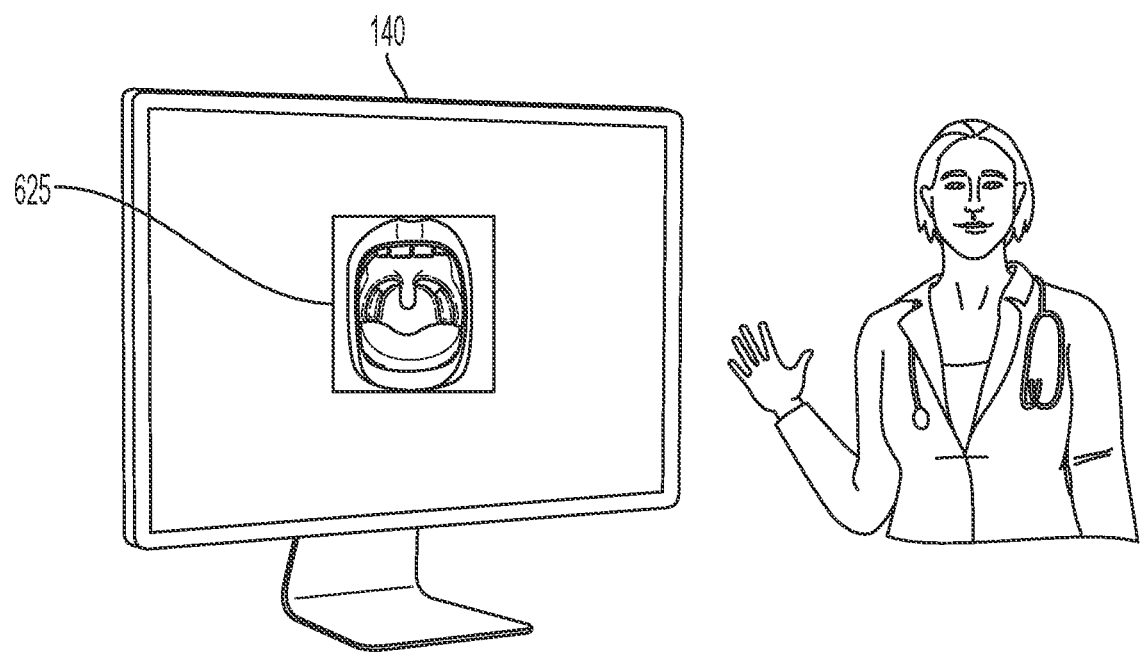

As shown in FIG. 6D, the user device 140 may display the diagnostic information of the user. In this way, the doctor may review the user's diagnostic information, and diagnose the user. For example, the doctor may input a clinical assessment via the user device 140. The user device 140 may provide the clinical assessment to the platform 130. In turn, the user device 120 may obtain the clinical assessment from the platform 130.

Figure 6E:
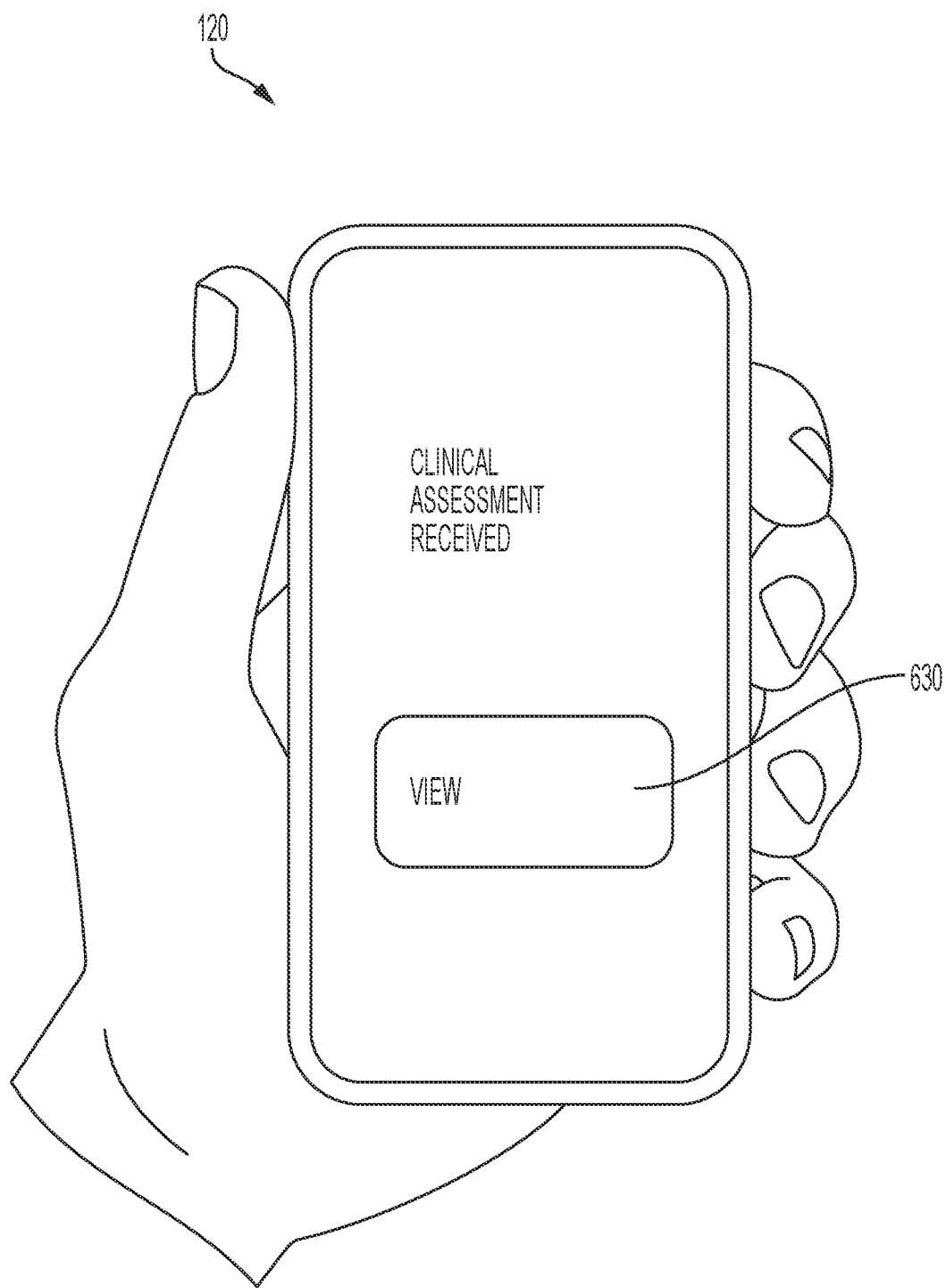

As shown in FIG. 6E, the user device 120 display information identifying that clinical assessment is available from the platform 130, and may display a user interface element 630 that permits the user to view the clinical assessment.

In this way, the user may select a doctor with whom the diagnostic information is to be accessible. Further, the user may select that the doctor be saved via the diagnostic application so that additional diagnostic information may be provided to the doctor in the future without requiring one or more of the steps shown in FIGS. 6A-6E.

FIGS. 7A-7C are diagrams of a user interface of the diagnostic application according to an embodiment.

As shown in FIG. 7A, the user device 120 may receive an input 705 via the user interface 500 that selects a user interface element 540 that identifies that the obtained diagnostic information is to be used to determine a clinical assessment. For example, the user may perform a touch gesture in association with the user interface element 540, and the user device 120 may receive the input 705 that identifies that the obtained diagnostic information is to be used to determine a clinical assessment.

As shown in FIG. 7B, and by reference numbers 710 and 715, the user device 120 may provide the diagnostic information to the platform 130 via the network 150. As shown by reference number 720, the platform 130 may determine a clinical assessment using the diagnostic information and a model. As shown by reference numbers 725 and 730, the platform 130 may provide the clinical assessment to the user device 120 via the network 150.

As shown in FIG. 7C, the user device 120 display information identifying that a clinical assessment is available from the platform 130, and may display a user interface element 735 that permits the user to view the clinical assessment.

In this way, the platform 130 may determine the clinical assessment using the diagnostic information and a model, and provide the clinical assessment to the user device 120. Accordingly, a user may obtain a clinical assessment without direct input from a doctor.

Figure 8:
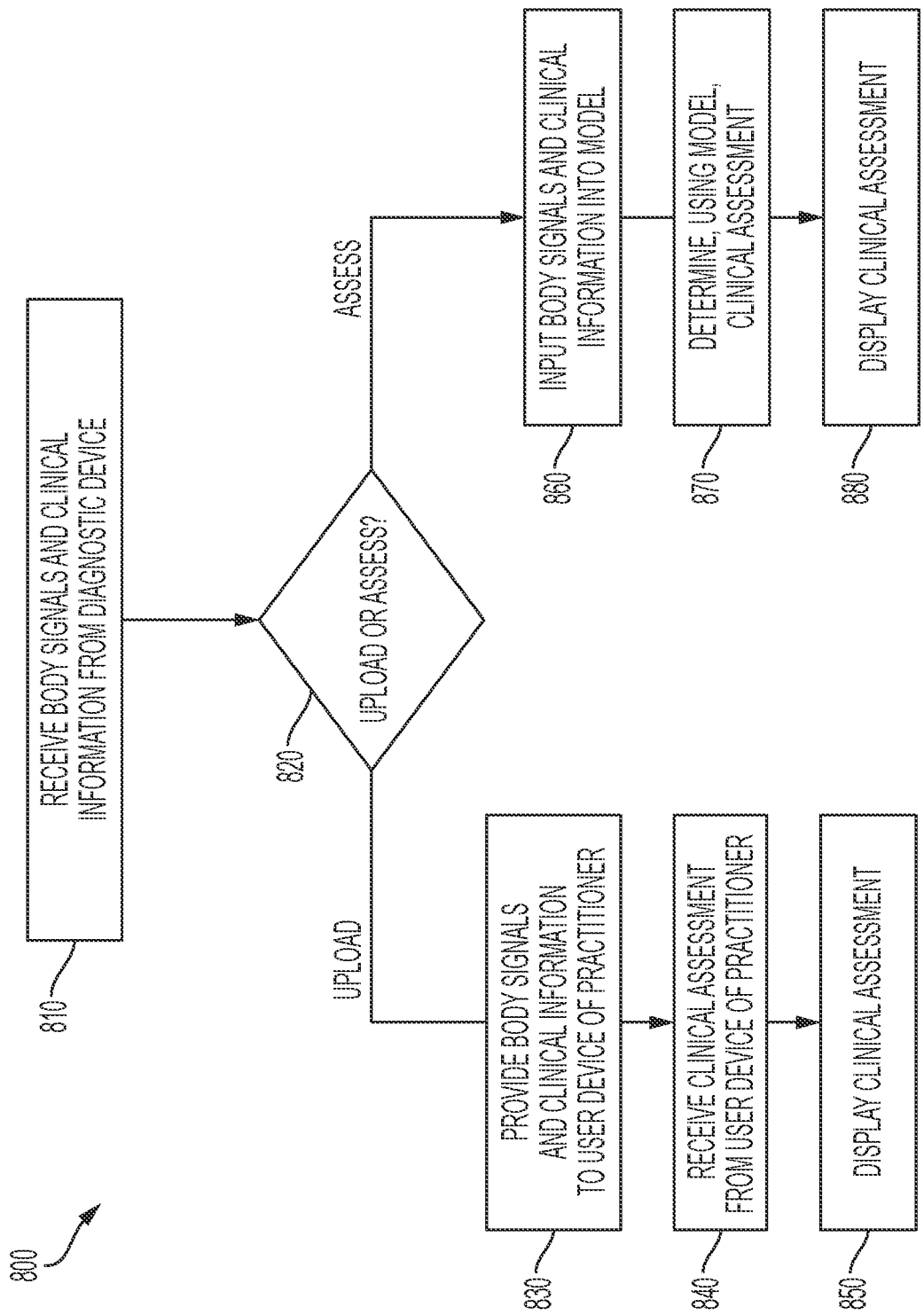
FIG. 8 is a flowchart of an example process of displaying a clinical assessment according to an embodiment.

FIG. 8 is a flowchart of an example process 800 of displaying a clinical assessment according to an embodiment.

In some embodiments, one or more operations of FIG. 8 may be performed by the user device 120. In other embodiments, one or more operations of FIG. 8 may be performed by another device or a group of devices separate from or including the user device 120, such as the diagnostic device 110, the platform 130, and/or the user device 140.

As shown in FIG. 8, the process 800 may include receiving body signals and clinical information from a diagnostic device (operation 810). For example, the user device 120 may receive body signals and clinical information from the diagnostic device 110. Additionally, the user device 120 may receive body signals and clinical information based on a user input to the user device 120.

The body signals may include bio-information of a user (e.g., an oxygen saturation level, a temperature, a heart rate, a blood pressure, a calorie level, etc.), audio information of the user (e.g., a heart sound, a lung sound, etc.), image or video information of the user, etc., obtained via the diagnostic device 110.

Additionally, the clinical information may include user information such as characteristic information of the user (e.g., a name, an address, an occupation, a marital status, a date of birth, a gender, a weight, a height, etc.), allergy information of the user, vaccination information of the user, chronic or pre-existing condition information of the user, health history information of the user, family health history information of the user, etc., obtained via the user device 120.

Further, the clinical information may identify one or more primary symptoms, and one or more sub-symptoms. The clinical information may identify a symptom, a location of the symptom, a severity of the symptom, a duration of the symptom, or the like.

The user device 120 may execute the diagnostic application, and receive the body signals and clinical information based on executing the diagnostic application. For example, the user may input clinical information via the user device 120. Additionally, the user may interface the user device 120 with the diagnostic device 110, and the user device 120 may receive the body signals and clinical information from the diagnostic device 110.

As further shown in FIG. 8, the process 800 may include determining whether the body signals and clinical information are to be uploaded to a platform or to be used to obtain a clinical assessment (operation 820). For example, based on receiving the body signals and clinical information, the user device 120 may determine whether body signals and clinical information are to be provided to the platform 130 for remote clinical assessment via the user device 140, or are to be used to determine a clinical assessment using a model. The user device 120 may perform the foregoing determination based on a user input via the user device 120.

As further shown in FIG. 8, if the body signals and clinical information are to be uploaded (operation 820— UPLOAD), then the process 800 may include providing body signals and clinical information to a user device of a practitioner (operation 830). For example, based on determining that body signals and clinical information are to be provided to the platform 130 for remote clinical assessment via the user device 140, the user device 120 may provide the body signals and clinical information to the user device 140 of the practitioner via the platform 130. In this way, the practitioner may review the body signals and clinical information, and input a clinical assessment to the user device 140. The user device 140 may provide the clinical assessment to the platform 130.

As further shown in FIG. 8, the process may include receiving a clinical assessment from the user device of the practitioner (operation 840). For example, the user device 120 may receive the clinical assessment from the user device 140 via the platform 130.

As further shown in FIG. 8, the process 800 may include displaying the clinical assessment. For example, the user device 120 may display the clinical assessment via the diagnostic application. In this way, the user may view the clinical assessment, and take appropriate measures.

As further shown in FIG. 8, if the first diagnostic information received from the diagnostic device is to be used to obtain a clinical assessment (operation 820—ASSESS), then the process 800 may include the body signals and clinical information into a model (operation 860).

The platform 130 may be configured to generate a model. The model may be configured to receive body signals and clinical information as an input, and generate a clinical assessment as an output. The model may receive any permutation of the body signals and clinical information described herein as an input, and determine a clinical assessment as an output.

The platform 130 may use machine learning and/or AI techniques to analyze data and generate the model. As used herein, the term "model" may refer to one more models. The techniques may include, for example, supervised and/or unsupervised techniques, such as artificial networks, neural networks, support vector machines, Bayesian statistics, learning automata, Hidden Markov Modeling, linear classifiers, quadratic classifiers, decision trees, association rule learning, computer vision, natural language processing, acoustic machine learning, or the like.

The platform 130 may generate the model by training the model using body signals and clinical information and a clinical assessment. For example, the platform 130 may receive body signals and clinical information that are associated with a known clinical assessment, and train the model based on body signals and clinical information that are associated with the known clinical assessment. Further, the platform 130 may generate the model by training the model using a loss function, such as a regression loss function (e.g., mean squared error, mean squared logarithmic error, mean absolute error, etc.), a binary classification loss function (e.g., binary cross-entropy, hinge loss, squared hinge loss, etc.) a multi-class classification loss function (e.g., multi-class cross-entropy loss, sparse multi-class cross-entropy loss, Kullback Leibler divergence loss, etc.), or the like.

The platform 130 may store the model based on generating the model, and may update the model using feedback information and/or additional body signals and clinical information that are associated with a clinical assessment. In some embodiments, the platform 130 may provide the trained model to the user device 120 in order to permit the user device 120 to utilize the model.

According to an embodiment, the model may be configured to receive image data of the user, and determine whether the user is healthy or diseased as the clinical assessment. As examples, the model may differentiate a healthy throat from a throat with a strep infection, and differentiate a normal eardrum from an infected eardrum.

According to an embodiment, the model may be configured to receive audio data of the user, and determine whether the user is healthy or diseased as the clinical assessment. As examples, the model may distinguish between healthy and diseased breathing in order to predict severity of asthma and airway obstruction from recordings of breath sounds (e.g., using audio analysis of breath sounds to predict degree of resistance from airway obstruction or filtering out/identifying adventitious or pathological lung sounds like wheezes or crackles), identify gastrointestinal motility based on stomach or bowel sound patterns, or identify cardiac conditions through identification of abnormal beats/rhythms or pathologic murmurs or gallops.

According to an embodiment, the model may receive image data and audio data of the user, and determine a degree of respiratory distress of the user as the clinical assessment. For example, the model may analyze video data of the user's breathing and audio data of the user's breathing/auscultation, and determine the degree of respiratory distress.

According to an embodiment, the model may receive reflective sound patterns (e.g., echo signals) of the user, and determine whether the user has an ear infection as the clinical assessment. For example, the diagnostic device 110 may emit a short sound wave to the ear. Based on the level of fluid buildup in the ear, the user's ear will return different sound patterns. The stethoscope 135 of the diagnostic device 110 may obtain the reflected sound patterns. The model may provide predictive scoring for fluid buildup to correlate with ear infections, based on the reflected sound patterns. The model may also receive image data of the user's ear as diagnostic information, and determine or confirm whether the user has an ear infection based on the image data and the audio data.

According to an embodiment, the model may receive thermal image information of the user, and determine a region or degree of inflammation as the clinical assessment.

According to an embodiment, the model may receive image information of the user, and determine a BMI and/or body composition (e.g., fat percentage, central adiposity, etc.) of the user as the clinical assessment.

According to an embodiment, the model may receive image information and audio information of the user, and determine a degree of pain or discomfort of the user as the clinical assessment. For example, the model may analyze changes in facial expressions and modulations in voice and sounds to predict degrees of pain or discomfort based on grimaces or facial expressions and/or hints of depression based on facial expressions or voice recognition patterns.

According to an embodiment, the model may use natural language processing, computer vision, acoustic machine learning, and data science to scan for keywords, clinical information, images, video, and audio accessed through the user and a physician portal during a telemedicine visit, and develop a disease score or decision support that will assist the physician validate their diagnosis and determine the appropriate treatment plan.

According to embodiments, the model may receive any permutation of the body signals and clinical information, and determine a clinical assessment based on body signals and clinical information. As examples, the model may receive only image information, only audio information, only body signals, image information and audio information, image information and body signals, audio information and body signals, or image information, audio information, and body signals as the diagnostic information. As additional examples, the model may receive only clinical information, clinical information and user characteristic information, clinical information and image information, clinical information and audio information, etc.

According to an embodiment, the model may determine a diagnosis of the user as the clinical assessment. For example, the diagnosis may correspond to a particular disease or ailment. According to an embodiment, the model may determine a severity of a diagnosis. For example, the severity may identify how severe the disease is and/or may identify whether further medical attention is suggested.

According to an embodiment, the model may determine a treatment as the clinical assessment. For example, the treatment may correspond to a drug to administer, a regiment to follow, an action to be performed, a hospital or clinic to visit, an intensification of a regiment, or the like.

Further, as the physicians create clinical assessments by synthesizing all relevant body signals, audiovisual data, and clinical data collected from users, this data will be anonymized and utilized to determine patterns and associations which lead to specific diagnoses and specific disease severity levels. Depending on a user's specific cluster of data gathered from the diagnostic device 110 the model may suggest the user's most likely diagnosis and also guide the user to the most appropriate level and type of treatment. In this way, some embodiments herein permit diagnosis without direct physician input and in the comfort of a user's home.

Although FIG. 8 shows example blocks of process 800, in some embodiments, process 800 may include additional operations, fewer operations, different operations, or differently arranged operations than those depicted in FIG. 8. Additionally, or alternatively, two or more of the blocks of process 800 may be performed in parallel.

The foregoing disclosure provides illustration and description, but is not intended to be exhaustive or to limit the embodiments to the precise form disclosed. Modifications and variations are possible in light of the above disclosure or may be acquired from practice of the embodiments.

As used herein, the term "component" is intended to be broadly construed as hardware, firmware, or a combination of hardware and software.

It will be apparent that systems and/or methods, described herein, may be implemented in different forms of hardware, firmware, or a combination of hardware and software. The actual specialized control hardware or software code used to implement these systems and/or methods is not limiting of the embodiments. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible embodiments. In fact, many of these features may be combined in ways not specifically recited in the claims and/or disclosed in the specification. Although each dependent claim listed below may directly depend on only one claim, the disclosure of possible embodiments includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A method of obtaining a clinical assessment of a user by a user device in communication with a hand-held diagnostic device comprising a wireless transceiver, a battery, and sensors including an endoscopic camera, a pulse oximeter, a temperature sensor, and a stethoscope, wherein the endoscopic camera comprises a lens, a photo tube configured to be inserted in the user's mouth, and an imaging sensor, the method comprising:

capturing, by the hand-held diagnostic device, imaging of a user's organs using at least one sensor in the hand-held diagnostic device, wherein the at least one sensor in the hand-held diagnostics device comprises the endoscopic camera and capturing the imaging of the user's organs is in real time;

streaming, by the hand-held diagnostic device, the imaging of the user's organs to the user device, wherein the streaming of the imaging of the user's organs is in real time;

visually displaying, by the user device, the imaging of the user's organs, wherein the visual displaying of the imaging of the user's organs is in real-time and enables remote viewing of the imaging of the user's organs that is captured by the hand-held diagnostic device in real-time;

receiving, by the user device, input from the user selecting a portion of the imaging of the user's organs as a first set of diagnostic information of the user, wherein the input is in response to the visual displaying and the remote viewing of the imaging of the user's organs in real-time;

measuring, by the hand-held diagnostic device, body signals using sensors in the hand-held diagnostics device, wherein the body signals of the user comprise at least one body sound;

obtaining, by the user device from the hand-held diagnostic device, the first set of diagnostic information of the user, wherein the first set of diagnostic information of the user comprises the portion of the imaging of the user's organs captured by the hand-held diagnostic device and the body signals measured by the hand-held diagnostic device;

obtaining, by the user device, a second set of diagnostic information comprising a set of clinical information comprising the user's (i) symptoms, (ii) medical history, and (iii) demographics;

obtaining, by the user device, input data indicating whether to provide the first set of diagnostic information and the second set of diagnostic information to generate the clinical assessment by a second user of a remote user device or to generate the clinical assessment by an artificial intelligence model;

in response to receiving the input data indicating to generate the clinical assessment by an artificial intelligence model, inputting, by the user device, the first set of diagnostic information and the second set of diagnostic information into the artificial intelligence model, the artificial intelligence model trained using the plurality of body signals and the set of clinical information obtained by the user device;

obtaining, using the trained artificial intelligence model, the clinical assessment of the user based on the plurality of body signals comprising at least one body sound; and visually displaying, on the user device in communication with the hand-held diagnostic device, the clinical assessment.

2. The method of claim 1, further comprising:

receiving, by the user device in communication with the hand-held diagnostic device, the imaging of the user's organs streamed from the hand-held diagnostic device, wherein the imaging of the user's organs comprises video captured by the endoscopic camera of the hand-held diagnostic device, based on the user manipulating the hand-held diagnostic device to obtain an image of a body part of the user; and visually displaying, by the user device in communication with the hand-held diagnostic device, in real time, the video captured by the endoscopic camera of the hand-held diagnostic device, wherein the visual displaying enables remote viewing of the video to permit the user to place the hand-held diagnostic device in proximity to the body part of the user while remotely viewing the video via the user device.

3. The method of claim 1, wherein the first set of diagnostic information further includes video information of the user.

4. The method of claim 1, wherein measuring, by the hand-held diagnostic device, the body signals of the user further includes measuring additional body signals comprising one or more of: a temperature of the user using the temperature sensor, an oxygen saturation of the user using the pulse oximeter sensor, respiration rate of the user, an electrocardiogram (ECG) of the user, a blood pressure of the user, or a heart rate of the user.

5. The method of claim 1, further comprising:

in response to receiving the input data indicating to generate the clinical assessment by the second user of a remote user device, providing, by the user device in communication with the hand-held diagnostic device and to a server, the first set of diagnostic information and the second set of diagnostic information to a remote user device, associated with the second user, to obtain the first set of diagnostic information and the second set of diagnostic information, wherein the second user is a physician and generates the clinical assessment; and obtaining, from the remote user device in communication with the user device and the server, the clinical assessment by the second user of a remote user device.

6. A system comprising:

a hand-held diagnostic device comprising a wireless transceiver, a battery, and sensors including an endoscopic camera, a pulse oximeter, a temperature sensor, and a stethoscope, the hand-held diagnostic device in communication with a user device and configured to:

capture, in real time, imaging of a user's organs using at least one sensor, wherein the at least one sensor comprises the endoscopic camera;

stream, in real-time, the imaging of the user's organs to the user device;

measure body signals using the sensors, wherein the body signals of the user comprise at least one body sound; and the user device, wherein the user device is configured to obtain a clinical assessment of a user, the user device comprising:

a memory configured to store instructions; and a processor configured to execute the instructions to:

control a display of the user device to visually display, in real-time, the imaging of the user's organs, wherein the visual displaying of the imaging of the user's organs enables remote viewing of the imaging of the user's organs that is captured by the hand-held diagnostic device in real-time;

receive input from the user selecting a portion of the imaging of the user's organs as a first set of diagnostic information of the user, wherein the input is in response to the visual displaying and the remote viewing of the imaging of the user's organs in real-time;

obtain, from the hand-held diagnostic device in communication with the user device, the first diagnostic information of the user, wherein the first set of diagnostic information of the user comprises the portion of the imaging of the user's organs captured by the hand-held diagnostic device and the body signals measured by the hand-held diagnostic device;

obtain, by the user device, second diagnostic information comprising clinical information comprising the user's: (i) symptoms, (ii) medial history, and (iii) demographics;

obtain, by the user device, input data indicating whether to provide the first diagnostic information and the second diagnostic information to generate the clinical assessment by a second user of a remote user device or to generate the clinical assessment by an artificial intelligence model;

in response to receiving the input data indicating to generate the clinical assessment by an artificial intelligence model, input the first diagnostic information and second diagnostic information obtained in the prior steps, into the artificial intelligence model trained using the plurality of body signals and the clinical information, wherein at least one body signal is a body sound;

obtain, on the user device in communication with the hand-held diagnostic device, the clinical assessment of the user from the trained artificial intelligence model, wherein the plurality of body signals obtained by the sensors of the hand-held diagnostic device and the clinical information of the user are obtained via the user device; and control the display of the user device in communication with the hand-held diagnostic device to visually display the clinical assessment to the user.

7. The system of claim 6, wherein the user device comprises the processor that is further configured to:
receive the imaging of the user's organs streamed from the hand-held diagnostic device, wherein the imaging of the user's organs comprises video captured by the endoscopic camera of the hand-held diagnostic device, based on the user manipulating the hand-held diagnostic device to obtain an image of a body part of the user; and
control the display to visually display, in real time, the video captured by the endoscopic camera of the hand-held diagnostic device, wherein the visual displaying enables remote viewing of the video to permit the user to place the hand-held diagnostic device in proximity to the body part of the user while remotely viewing the video via the user device in communication with the hand-held diagnostic device.

8. The system of claim 6, wherein the first diagnostic information further includes video information of the user.

9. The system of claim 6, wherein the hand-held diagnostic device further measures additional body signals of the user comprising one or more of: a temperature of the user using the temperature sensor, an oxygen saturation of the user using the pulse oximeter sensor, a respiration rate of the user, an electrocardiogram (ECG) of the user, a blood pressure of the user, or a heart rate of the user.

10. The system of claim 6, wherein the user device comprises the processor that is further configured to: in response to receiving the input data indicating to generate the clinical assessment by the second user of a remote user device, provide, to a server, the first diagnostic information and the second diagnostic information to a remote user device in communication with the server, associated with the second user to obtain the first diagnostic information and the second diagnostic information, wherein the second user is a physician and generates the clinical assessment; and
obtain, from the remote user device in communication with the server, the clinical assessment by the second user of the remote user device.

11. A non-transitory computer-readable medium storing instructions, the instructions comprising: instructions that, when executed by one or more processors of a system, causes the one or more processor to:
capture, by a hand-held diagnostic device in communication with a user device, imaging of a user's organs using sensors in the hand-held diagnostic device, wherein the hand-held diagnostic device comprises a wireless transceiver, a battery, and sensors including an endoscopic camera, a pulse oximeter, a temperature sensor, and a stethoscope, and is configured to obtain a clinical assessment of a user and capturing the imaging of the user's organs is in real time;
stream, by the hand-held diagnostic device, the imaging of the user's organs to the user device, wherein the streaming of the imaging of the user's organs is in real time;
visually display, by the user device, the imaging of the user's organs, wherein the visual displaying of the imaging of the user's organs is in real-time and enables remote viewing of the imaging of the user's organs that is captured by the hand-held diagnostic device in real-time;
receive, by the user device, input from the user selecting a portion of the imaging of the user's organs as a first set of diagnostic information of the user, wherein the input is in response to the visual displaying and the remote viewing of the imaging of the user's organs in real-time;
measure, by the hand-held diagnostic device, body signals using sensors in the hand-held diagnostics device, wherein the body signals of the user comprise at least one body sound;
obtain, from the hand-held diagnostic device in communication with the user device, the first diagnostic information of the user, wherein the first set of diagnostic information of the user comprises the portion of the imaging of the user's organs captured by the hand-held diagnostic device and the body signals measured by the hand-held diagnostic device;
obtain, from the hand-held diagnostic device, second diagnostic information comprising clinical information comprising one or more of the user's: (i) symptoms, (ii) medical history and (iii) demographics;
obtain, by the user device, input data indicating whether to provide the first diagnostic information and the second diagnostic information to generate the clinical assessment by a second user of a remote user device or to generate the clinical assessment by an artificial intelligence model;
in response to receiving the input data indicating to generate the clinical assessment by an artificial intelligence model, input the first diagnostic information and second diagnostic information into the artificial intelligence model, the artificial intelligence model trained using the plurality of body signals and the clinical information;
obtain the clinical assessment of the user from the trained artificial intelligence model, the plurality of body signals obtained by the sensors and the clinical information of the user obtained by the user device input into the artificial intelligence model; and
control a display of the user device to visually display the clinical assessment to the user.

12. The non-transitory computer-readable medium of claim 11, wherein the one or more instructions further cause the one or more processors to:
receive, from the hand-held diagnostic device, the imaging of the user's organs streamed from the hand-held diagnostic device, wherein the imaging of the user's organs comprises video captured by the endoscopic camera of the hand-held diagnostic device, based on the user manipulating the hand-held diagnostic device to obtain an image of a body part of the user; and
control the display to visually display, in real time, the video captured by the endoscopic camera of the hand-held diagnostic device, wherein the visual displaying enables remote viewing of the video to permit the user to place the hand-held diagnostic device in proximity to the body part of the user while remotely viewing the video via the user device.

13. The non-transitory computer-readable medium of claim 11, wherein the first diagnostic information further includes video information of the user.

14. The non-transitory computer-readable medium of claim 11, wherein the body signals of the user further include a temperature of the user, an oxygen saturation of the user, a respiration rate of the user, an electrocardiogram (ECG) of the user, a blood pressure of the user, or a heart rate of the user.

15. The method of claim 1, wherein the hand-held diagnostic device further comprises at least one of a microphone, a digital stethoscope, a variable focus camera, an infrared temperature sensor, an EKG sensor, or a blood pressure sensor.

16. The method of claim 1, wherein the hand-held diagnostic device includes at least one of a microphone, an EKG sensor, an infrared temperature sensor, or a blood pressure sensor.

17. The method of claim 15, wherein the hand-held diagnostic device incorporates a detector that includes one or more photodetectors and offers colorimetric readouts.

18. The method of claim 17, wherein the detector can detect light or colorimetric changes from an accompanying single-use chip or wafer pre-loaded with material-based nanoparticles that can bind to infectious agents, body fluids, or hormones.

19. The method of claim 17, wherein the hand-held diagnostic device further comprises a stand-alone separate housing chamber in which a chip or wafer, a reagent, and test accessories are incorporated.

20. The method of claim 19, wherein the chip or wafer provides at least one of a fluorescent or bioluminescent optical readout or a colorimetric readout.

21. The method of claim 20, wherein the reagent is in a liquid format or in a dissolvable lyophilized dried powder format.

22. The method of claim 20, wherein the stand-alone separate housing chamber is sealed to prevent contamination and tampering.

23. The method of claim 1, wherein the first diagnostic information includes test measurements regarding a body fluid sample of the user.

24. The method of claim 1, wherein the at least one body sound includes recorded sounds of user breathing, heartbeat, or stomach.

25. The method of claim 1, wherein the endoscopic camera is configured to image at a focal distance in a range of 20 mm to 100 mm.

26. The non-transitory computer-readable medium of claim 11, wherein the one or more instructions further cause the one or more processors to:

in response to receiving the input data indicating to generate the clinical assessment by the second user of the remote user device, provide, to a server, the first diagnostic information and the second diagnostic information to the remote user device in communication with the server, associated with the second user, to obtain the first diagnostic information and the second diagnostic information, wherein the second user is a physician and generates the clinical assessment; and obtain, from the remote user device in communication with the server, the clinical assessment by the second user of the remote user device.

* * * * *